United States Patent
Bonnette et al.

(10) Patent No.: US 6,764,483 B1
(45) Date of Patent: Jul. 20, 2004

(54) THROMBECTOMY CATHETER AND SYSTEM

(75) Inventors: Michael J. Bonnette, Minneapolis, MN (US); John Edward Morris, Minneapolis, MN (US); Steven E. Wiesel, Montrose, MN (US); John B. Bridgeman, Minneapolis, MN (US); Debra M. Kozak, Forest Lake, MN (US); Rosemary C. Beaupre, Lino Lake, MN (US); Mark L. Jenson, Greenville, MN (US); Cindy M. Setum, Plymouth, MN (US); Robert C. Dutcher, Maple Grove, MN (US)

(73) Assignee: Possis Medical, Inc., Minneapolis, MN (US)

( * ) Notice: Subject to any disclaimer, the term of this patent is extended or adjusted under 35 U.S.C. 154(b) by 0 days.

(21) Appl. No.: 09/915,875

(22) Filed: Jul. 26, 2001

Related U.S. Application Data

(62) Division of application No. 09/417,395, filed on Oct. 13, 1999, now Pat. No. 6,676,627, which is a continuation-in-part of application No. 08/349,665, filed on Oct. 5, 1994, now Pat. No. 6,558,366, which is a division of application No. 08/006,076, filed on Jan. 15, 1993, now Pat. No. 5,370,609, which is a continuation of application No. 07/563,313, filed on Sep. 6, 1990, now abandoned.

(51) Int. Cl.$^7$ .............................................. A61M 5/178
(52) U.S. Cl. .................. 604/507; 604/500; 604/22; 604/35; 604/43; 606/159
(58) Field of Search ................................ 604/22, 43, 35, 604/27, 48, 118, 119, 19, 264, 523–527, 500, 506, 507–509; 606/127, 128, 159, 190, 167, 170, 194, 180; 134/167 C, 168 C, 167 R, 172; 433/96; 239/214.15

(56) References Cited

U.S. PATENT DOCUMENTS

| | | | | |
|---|---|---|---|---|
| 4,950,238 A | * | 8/1990 | Sullivan | 604/22 |
| 5,318,518 A | * | 6/1994 | Plechinger et al. | 604/43 |
| 6,096,001 A | * | 8/2000 | Drasler et al. | 604/22 |

* cited by examiner

*Primary Examiner*—Brian L. Casler
*Assistant Examiner*—Cris L. Rodriguez
(74) *Attorney, Agent, or Firm*—Hugh D. Jaeger

(57) ABSTRACT

Cross stream thrombectomy catheter and system for fragmentation and removal of thrombus or other material from blood vessels or other body cavities. High velocity saline jets emitted from a toroidal loop jet emanator or other jet emanator in a catheter distal end entrain fluid through inflow orifices, and with flow resistances create a back-pressure which drives cross stream streams through outflow orifices in a radial direction and thence radially and circumferentially to apply normal and drag forces on thrombotic deposits or lesions in the blood vessel or other body cavity, thereby breaking apart and transporting thrombus particles to be entrained through the inflow orifices, whereupon the high velocity jets macerate the thrombus particles which then transit an exhaust lumen or recirculate again via the outflow orifices.

4 Claims, 26 Drawing Sheets

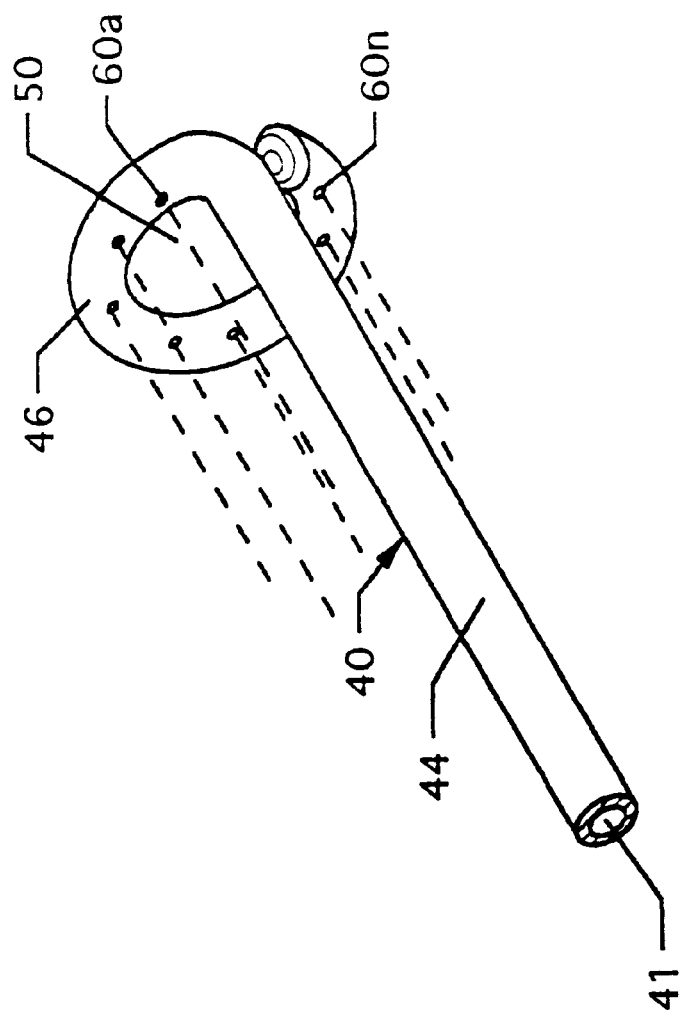

THROMBECTOMY CATHETER AND SYSTEM

CROSS REFERENCES TO CO-PENDING APPLICATIONS

This patent application is a divisional of Ser. No. 09/417,395 filed Oct. 13, 1999 now U.S. Pat. No. 6,676,627, which is a continuation-in-part of Ser. No. 08/349,665 filed Dec. 5, 1994 now U.S. Pat. No. 6,558,366, which is a divisional of Ser. No. 08/006,076 filed Jan. 15, 1993, Pat. No. 5,370,609, which is a continuation of Ser. No. 07/563,313 filed Aug. 6, 1990, abandoned.

BACKGROUND OF THE INVENTION

1. Field of the Invention

The present invention relates to apparatus for use in treatment of the human body. More particularly, the present invention relates to an elongated device which may be a single catheter assembly or a multiple component catheter assembly and which is suitable for use through percutaneous or other access, for endoscopic procedures, or for intraoperative use in either open or limited access surgical procedures. Still more particularly, the present invention relates to an elongated device in the form of a waterjet thrombectomy catheter, hereinafter termed cross stream thrombectomy catheter, for fragmentation and removal of thrombus or other unwanted material from blood vessels or body cavities that uses high velocity saline (or other suitable fluid) jets to macerate the thrombus or other unwanted material. The elongated device bears certain similarities to known waterjet thrombectomy catheter constructions but differs therefrom in several material respects, a major distinction being in the provision of means which produce cross stream jets to create a recirculation flow pattern optimized for clearing a large cross section of mural thrombus or other similar material, the name cross stream thrombectomy catheter deriving from this major distinction. Further, the present invention also relates to a system constituted either by the combination of the elongated device with both pressurized fluid source means and exhaust regulation means or by the combination of the elongated device with only pressurized fluid source means.

2. Description of the Prior Art

Waterjet thrombectomy catheters have been described in which a distal-to-proximal-directed waterjet(s) flow(s) past a window, orifice or gap at the distal end of the catheter, reentering the catheter and pushing flow through an evacuation lumen. When placed in a vessel containing thrombus and activated, the high velocity jet(s) will entrain surrounding fluid and thrombus into the window, orifice or gap region, where the high shear forces of the jet(s) will macerate the thrombus. The macerated particles will be removed from the body by the pressure generated on the distal end of the evacuation lumen by the impingement of the high velocity waterjet(s).

A limitation of these waterjet thrombectomy catheters has been the inability to remove organized, wall-adherent thrombus from large vessels. In accordance with the present invention, a cross stream thrombectomy catheter is described which overcomes this limitation by optimizing the recirculation pattern at the tip of the catheter to increase the drag force exerted on the mural thrombus to break it free from the vessel wall and allow it to be removed by the catheter.

SUMMARY OF THE INVENTION

The thrombectomy effect of waterjet thrombectomy catheters has been described as using the Venturi effect to create suction at the tip of the catheter to draw thrombus into the waterjets where it is then macerated and evacuated through an exhaust lumen. However, when operating in a relatively large blood vessel, the fluid velocities in the vessel decrease rapidly as the distance from the jet increases, so that at the wall of the vessel there is a minimal amount of pressure gradient to push the thrombus towards the low pressure area of the catheter. Thus, a different force is needed to remove mural thrombus, and that source is fluid drag. Drag on a surface is proportionate to the velocity gradient at that surface. Thus, in order to maximize the drag force, the velocity gradient at the surface must be maximized.

The catheter described herein is provided with outflow means and inflow means and is designed to optimize the drag force on the surface of the vessel by synergistically utilizing inflows and outflows at the catheter tip to create a recirculation pattern. Since the blood vessel can be considered as an open system, the geometric arrangement of the outflow means and inflow means is critical to the maximization of the drag force at the wall of the vessel. Since the catheter is designed to be easily advanced axially through a blood vessel, and axial flows are more likely to dissipate before contributing greatly to recirculation, the flow vectors in the recirculation most important for creating efficient thrombectomy are in the circumferential and radial direction. Radial high velocity flow vectors are created by maximizing the flow through one or more outflow orifices where the one or more outflow orifices are designed to aim the flow perpendicular to the axis of the catheter. Circumferential high velocity flow vectors are created by the demand for entrained fluid by one or more inflow orifices and are supplied substantially from the one or more outflow orifices, with change in fluid flow direction near the vessel wall to return to the catheter.

In the preferred embodiment of the catheter, there is provided inflow means in the form of one or more inflow orifices located in an exhaust tubular means adjacent and proximal to a jet emanator means in the form of a toroidal loop jet emanator located distally on a jet body. One or more high velocity saline (or other suitable fluid) jets emanate from the toroidal loop jet emanator; these high velocity jet(s) entrain fluid, drawing flow into the inflow orifices, and can macerate thrombus drawn near the jet(s). One or more of the high velocity jets can be oriented to aid in the exhaust of macerated thrombotic material through the exhaust tubular means. Multiple inflow orifices may be formed around the circumference of the exhaust tubular means in a single axial plane. An oval-shaped inflow orifice in which the major axis lies parallel to the axis of the catheter is preferred to offer an inflow orifice as large as possible without compromising the area for inflow and the structure of the exhaust tubular means. There is also provided outflow means in the form of one or more outflow orifices located in the exhaust tubular means near the one or more inflow orifices. Multiple outflow orifices may be formed around the circumference of the exhaust tubular means in a single axial plane. Preferably, the outflow orifice(s) are located proximal to the inflow orifice(s). The outflow orifice(s) are usually located but not are limited to being located in close proximity to the inflow orifice(s). The size and quantity of the outflow orifices are determined to maximize the momentum leaving the outflow orifices while not compromising the structural integrity of the exhaust tubular means. The high velocity jets and entrained fluid create an internal pressure near the tip of the catheter. This internal pressure is partially "vented" by the outflow orifice(s). Too small of an area of the outflow orifice(s) will minimize the outflow flow rate and risk plugging of the orifice(s) by macerated thrombotic material, whereas too large of an outflow area will weaken the radial flow vector of the outflow and may reduce the ability of the catheter to exhaust the macerated thrombotic material by allowing the internal pressure at the tip to be reduced to the point that there is no driving force for the exhaust. An alternative embodiment can be made in which outflow and inflow orifices are located in the same axial plane, where the direction of flow through the orifices is determined by fluid mechanical factors, e.g., non-symmetric distributions of jets near the orifices. While single inflow and outflow orifices (or a combination inflow/outflow orifice) can be used, having multiple inflow and outflow orifices helps to create effective recirculation on all sides of the catheter, avoiding the problem of having a single orifice blocked by the vessel wall or being oriented away from the deposit.

Though not required for most applications, isolation means can be utilized, either incorporated into the catheter, or as a separate device, to isolate the portion of the blood vessel near the catheter tip during use. Isolation means can include balloons, filters, baskets, membranes, blood pressure modification, fluid flow control, or other occlusion devices such as are known in the art. Isolation means can limit passage of debris in the blood vessel, limit the flow of blood in the area of the catheter, or confine the recirculation area near the catheter tip.

The preferred operation mode of the device is such that the exhaust is regulated to be equivalent to the flow rate of the high velocity saline supply. Another embodiment of the device can be one in which no exhaust is designed in the catheter, so that it becomes one that macerates the thrombus into particles small enough to pass through the distal vasculature without significant blockage.

The preferred embodiment of the catheter also uses a radio-opaque marker coil aligned in a tapered and flexible tip assembly welded or otherwise suitably attached to the toroidal loop jet emanator at the distal end of the jet body. The radio-opaque marker coil is imbedded in the wall of the tapered and flexible tip in alignment with an exhaust lumen in the exhaust tubular means to provide structural integrity to the device so that the orientation of the jet(s) with respect to the inflow orifice(s) remains constant as the device is advanced and torqued in the anatomy. This tapered flexible radio-opaque marker coil tip can also be used as a flexible base in which a preferentially shaped tip can be mechanically or adhesively affixed so as to produce an atraumatic tip which could also aid in tracking and insertion.

Alternative embodiments of the present invention include jet emanator means having jet orifice(s) in a formed tubular passage, but the tubular passage is not formed into a toroidal loop as in the preferred embodiment. The formed tubular passage can be a metal tube bent into a "J", "L" or "U" shape, or a manifold or other chamber with at least one orifice through which fluid emanates as jet(s). The key features of inflow orifice(s) through which fluid passes as it is entrained by the jet(s), and the outflow orifice(s) through which some of this entrained fluid flows, provides non-axial flow for increased recirculation, and drag again provides enhanced thrombus removal.

One significant aspect and feature of the present invention is a thrombectomy catheter having cross stream from one or more outflow orifices for recirculating, creating normal and drag forces, and displacing the thrombus off the vessel wall and into one or more inflow orifices and having high velocity jets for macerating the thrombus.

Another significant aspect and feature of the present invention is the flow of the outflow jet(s) in a radial direction followed by circumferential flow whereupon which entrained thrombotic particles enter the inflow orifice(s) to be further macerated and exhausted through an exhaust lumen.

An optional feature of the present invention is a tapered and flexible tube assembly secured to a toroidal loop jet emanator at one end of a hypo-tube to maintain orientation of a jetted solution in an exhaust lumen and with respect to the inflow orifice(s) as the device is advanced and torqued in the anatomy.

Another significant aspect and feature of the present invention is the entrainment of fluid by the high velocity jet(s) through one or more inflow orifices providing a source of additional flow and a localized region of higher pressure for driving flow outward through one or more outflow orifices. This flow, and the associated recirculation and drag forces, provide a synergistic effect which greatly increases the effectiveness of the device over what would be expected without the flow recirculation.

Another significant aspect and feature of the present invention is that the aforementioned flow via the outflow orifice(s) provides the enhanced effectiveness without the need for complicated, expensive, or space consuming additional components, tubings or passageways. The enhanced effectiveness resulting from inflow and outflow orifices, improved recirculation, and vessel wall drag can extend the useful range of the device; the greatly enhanced ability to remove blood vessel deposits can allow lower source pressures to be used than otherwise would be required; and improved function provides for useful application in larger vessels or cavities than would otherwise be practical, even with a small, flexible catheter.

Another significant aspect and feature of the present invention is that recirculation via the inflow orifice(s) provides improved function without damage to the vessel wall which could be caused by a large opening adjacent the jet(s) allowing the vessel wall to be pulled into the large opening. The device offers enhanced effectiveness without significant trauma to the vessel wall, even when operated at high pressures, with 10,000 cm/s to 25,000 cm/s jet velocities, for example.

Having thus described embodiments of the present invention, it is the principal object of the present invention to provide a cross stream thrombectomy catheter.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein:

FIG. 4a illustrates an isometric view of a toroidal loop jet emanator;

DETAILED DESCRIPTION OF THE PREFERRED EMBODIMENTS

Figure 1A:
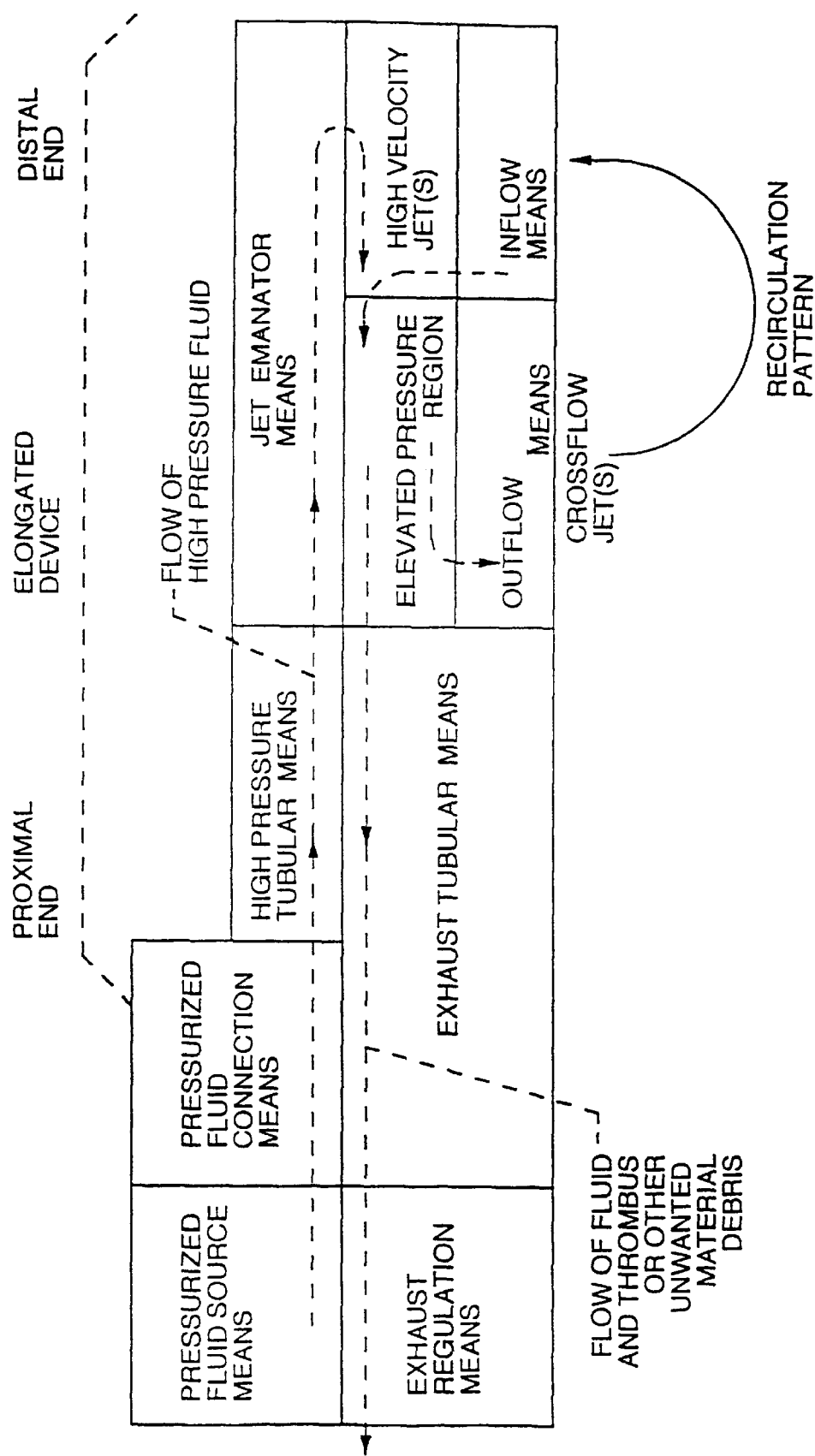
FIG. 1A illustrates in block diagram form a cross stream thrombectomy catheter system according to one embodiment of the present invention showing the interrelation of the various functional means thereof.

FIG. 1A illustrates in block diagram form a cross stream thrombectomy catheter system according to one embodiment of the present invention showing the interrelation of the various functional means thereof for use in removing thrombus or other unwanted material from a body vessel or cavity.

The major components of the system include an elongated device in the form of a cross stream thrombectomy catheter, a pressurized fluid source means, and, optionally, an exhaust regulation means connected to a collection system (not shown).

The elongated device includes first and second tubular means each having a proximal end and a distal end. The first tubular means is in the form of a high pressure tubular means having pressurized fluid connection means providing a fluid connection permanently or detachably coupled to its proximal end and jet emanator means at its distal end, the pressurized fluid connection means being connectible to the pressurized fluid source means. The second tubular means is in the form of either an exhaust tubular means, as shown, or other tubular means (not shown in FIG. 1A but described in detail in relation to FIGS. 18 and 19) which serves as an alternative to an exhaust tubular means in those instances when exhausting is not necessary or desired. When in the form of an exhaust tubular means, the second tubular means is usually associated with exhaust regulation means, although an exhaust regulation means is not essential. Whether in the form of an exhaust tubular means or other tubular means, the second tubular means includes outflow means and inflow means which in concert with high velocity jet(s) produced by the jet emanator means create cross stream jet(s) that establish a flow recirculation pattern.

The outflow means consists of one or more outflow orifices through which saline, blood or other fluid or a mixture thereof with macerated thrombus or other unwanted material debris flows from a region of higher pressure within the exhaust tubular means or other tubular means to outside the exhaust tubular means or other tubular means. The outflow orifices(s) are typically somewhat downstream from the high velocity region of the high velocity jet(s) where the velocities are lower and the mass flow rate is greater due to entrained fluid; and flow of fluid with or without macerated debris typically flows through the outflow orifice(s) with a component in the radial direction, creating cross stream jet(s). The outflow orifices may be round, elliptical, conical, slits, gaps between components, or other shape or design.

The inflow means consists of one or more inflow orifices through which the high velocity jet(s) draw in by fluid entrainment blood or other fluid from a body vessel or cavity, including thrombus or other unwanted material which may be present in the blood or other fluid. The inflow orifice(s) are typically near the high velocity region of the high velocity jet(s) where entrainment forces are great. The inflow orifices may be round, elliptical, conical, slits, gaps between components, or other shape or design.

The high pressure tubular means comprises an elongated structure having at least one passage or lumen along the length thereof suitable for passage of high pressure fluid. The elongated structure can be tubing with a circular or non-circular cross section and can be made of high strength polymeric material such as polyimide, metallic material such as stainless steel or titanium, or composite material such as fiber-reinforced material or a layered structure composed of layers of different materials.

The exhaust tubular means comprises an elongated structure having at least one passage or lumen along the length thereof suitable for passage of fluid and thrombus or other unwanted material debris. The elongated structure can be tubing with a circular or non-circular cross section and can be made of polymeric material such a polyethylene, polyester, polyurethane, or polyether block amide, high strength polymeric material such as polyimide, metallic material such as stainless steel or titanium, or composite material such as fiber-reinforced polymeric material or a layered structure composed of layers of different materials. Further, the elongated structure may have an attached structure near its distal end such as a chamber or manifold to accommodate the outflow means and the inflow means.

The other tubular means comprises an elongated structure having at least one passage or lumen along the length thereof suitable for passage of fluid. The elongated structure can be tubing with a circular or non-circular cross section or may resemble a shorter chamber such as a manifold, molded or constructed of multiple components. Suitable materials for the other tubular means are polymeric material such as polyethylene, polyester, or polyurethane, high strength polymeric material such as polyimide, metallic material such as stainless steel or titanium, or composite material such as fiber-reinforced polymeric material or a layered structure composed of layers of different materials.

If desired, isolation means (not shown) can be provided as part of the elongated device to isolate the region of the body vessel or cavity being treated, although this is not always required. Isolation means can include balloons, filters, baskets, membranes, blood pressure modification, fluid flow control, or other occlusion devices such as are known in the art. Isolation means can limit passage of debris in the blood vessel, limit the flow of blood in the area of the elongated device, or confine the recirculation area. Also if desired, additional tubular means can be provided for communication between the proximal end and the distal end of the elongated device, such as for passage of fluid or other material or for passage of devices such as guidewires, catheters, or imaging tools, or for actuation of isolation means, for inflation of a balloon, or for passage of medication or body fluids. The additional tubular means (not shown) comprises an elongated structure having at least one passage or lumen along the length thereof; for example, the elongated device can include a multiple-lumen tube, in which one lumen functions as the high pressure tubular means, a second lumen functions as the exhaust tubular means, and one or more additional lumens function as the additional tubular means which communicates between the proximal and distal ends of the elongated device.

The pressurized fluid source means includes fluid such as saline and one or more pumps or pressure intensifiers or pressurized fluid containers for delivering the fluid under pressure to the high pressure tubular means through the pressurized fluid connection means coupled to the proximal end thereof. The fluid can be provided at a single pressure or at multiple pressures, at variable or adjustable pressure, and at a steady flow or unsteady flow such as pulsatile flow.

The exhaust regulation means, when present, comprises structural components which increase, decrease, limit, or adjust the rate of flow of fluid and thrombus or other unwanted material debris along the exhaust tubular means and can be one or more pumps such as roller pumps or peristaltic pumps, clamps, restrictors, or other devices to influence the fluid flow rate. The exhaust regulation means can regulate exhaust at a predetermined or user-adjustable flow rate which can be correlated with or independent of the rate of flow of the pressurized fluid flowing along the high pressure tubular means. Further, the exhaust regulation means can have pressure measurement or flow rate measurement capabilities. The exhaust regulation means is connected to a suitable collection system (not shown).

The system is placed in operation by inserting the elongated device into a body vessel or cavity and advancing it to a site of thrombus or other unwanted material in the body vessel or cavity. Then the proximal end of the elongated device is connected to the pressurized fluid source means which provides pressurized saline (or other biologically compatible fluid) to the proximal end of the high pressure tubular means via the pressurized fluid connection means. At the distal end of the high pressure tubular means, pressurized saline (or other fluid) passes into the jet emanator means which produces high velocity saline (or other fluid) jet(s). The high velocity saline (or other fluid) jet(s) entrain blood or other fluid from the body vessel or cavity and draw it into the distal portion of the elongated device through the inflow means, carrying thrombus or other unwanted material from the body vessel or cavity along with the blood or other fluid. The high velocity saline (or other fluid) jet(s) together with the entrained blood or other fluid create a region of elevated pressure in the elongated device; this region of elevated pressure communicates with or is a part of the distal portion of the exhaust tubular means. The elevated pressure in the elevated pressure region drives fluid flow through the outflow means, creating cross stream jet(s) which have a radial component and may have circumferential and/or axial component(s) as well. The fluid in the elevated pressure region includes saline (or other fluid) from the high velocity jet(s) as well as the entrained blood or other fluid from the body vessel or cavity. The cross stream jet(s) impart normal and drag forces on thrombus or other unwanted material in the body vessel or cavity and greatly improve the effectiveness of the device in removing and breaking apart thrombus or other unwanted material which may be adhered to the body vessel or cavity, and form a recirculation pattern which further aids in drawing thrombus or other unwanted material towards the inflow means. The combination of outflow means, cross stream jet(s), recirculation pattern, inflow means, and high velocity jet(s) synergistically acts to provide for enhanced breakup and removal of thrombus or other unwanted material. The elevated pressure in the elevated pressure region can also aid in the transport of fluid and thrombus or other unwanted material debris through the exhaust tubular means. If desired, the rate of flow of fluid and thrombus or other unwanted material regulated by providing exhaust regulation means, although this is not always required.

Figure 1B:
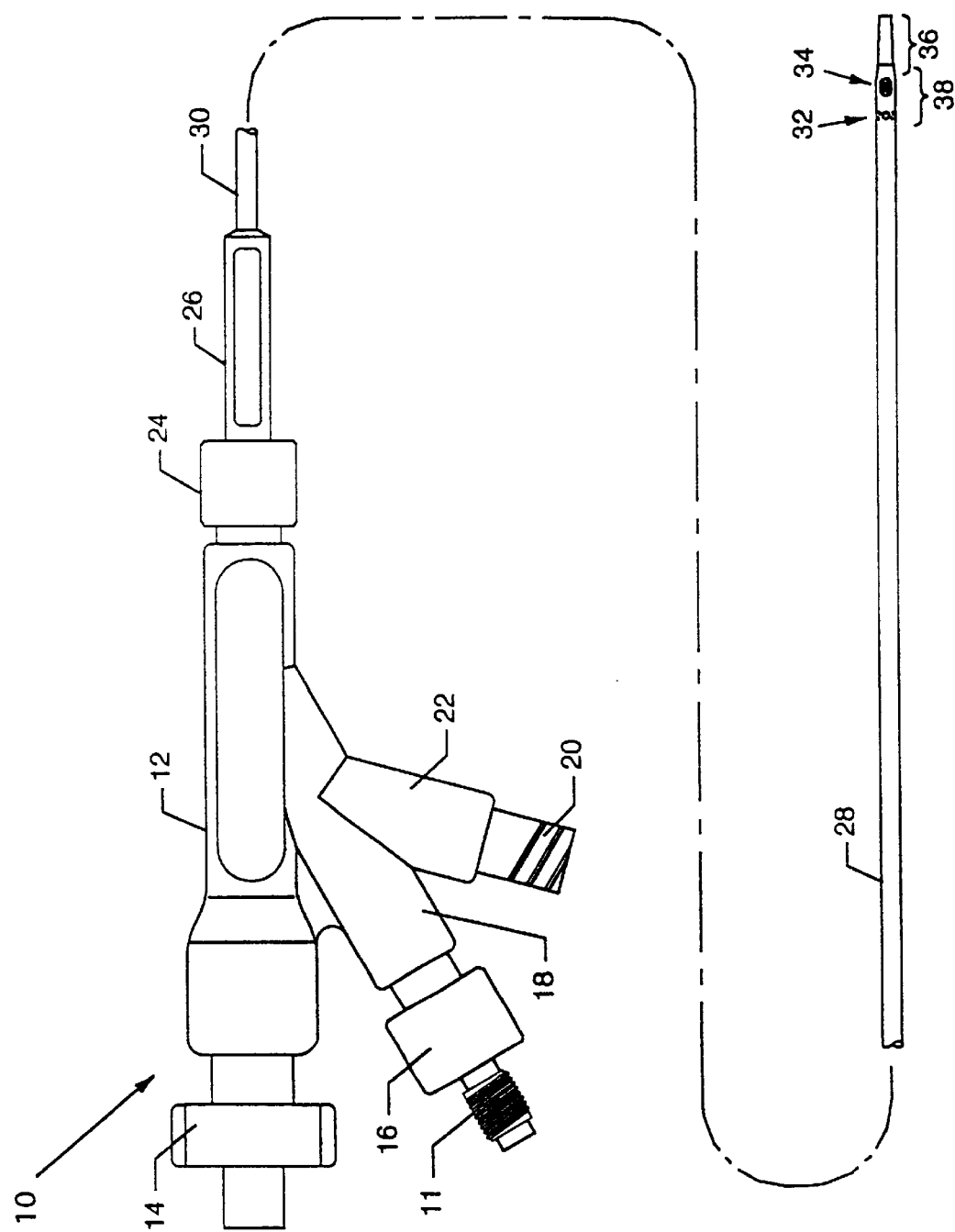
FIG. 1B illustrates a side view of an elongated device in the from of a cross stream thrombectomy catheter with provision for exhaust.

FIG. 1B illustrates a side view of an elongated device in the form of a cross stream thrombectomy catheter with exhaust provision 10 useful for the removal of thrombus. Externally visible components, or portions of components, of the cross stream thrombectomy catheter 10 include a manifold 12, a hemostasis unit 14 secured in the proximal end of the manifold 12, pressurized fluid connection means in the form of a threaded high pressure connection 11 and a Luer fitting 16 located at the proximal end of an angled manifold branch 18 extending from the manifold 12 for coupling to the pressurized fluid source means, a Luer connection 20 for coupling to exhaust regulation means located at the proximal end of another angled manifold branch 22 extending from the manifold branch 18, a Luer fitting 24 secured to the distal end of the manifold 12, a strain relief 26 secured to the distal end of the manifold 12 by the Luer fitting 24, exhaust tubular means in the form of an exhaust tube 28 having a proximal end 30 secured to the manifold 12 by the strain relief 26 and Luer fitting 24, outflow means in the form of one or more distally located outflow orifices 32 at the distal end 38 of the exhaust tube 28, inflow means in the form of one or more distally located inflow orifices 34 at the distal end 38 of the exhaust tube 28, and a tapered and flexible tip assembly 36 located at and aligned to and attached, as later described and illustrated, to the distal end of a jet emanator means in the form of a toroidal loop jet emanator residing in as well as being attached to the distal end 38 of the exhaust tube 28.

Figure 2:
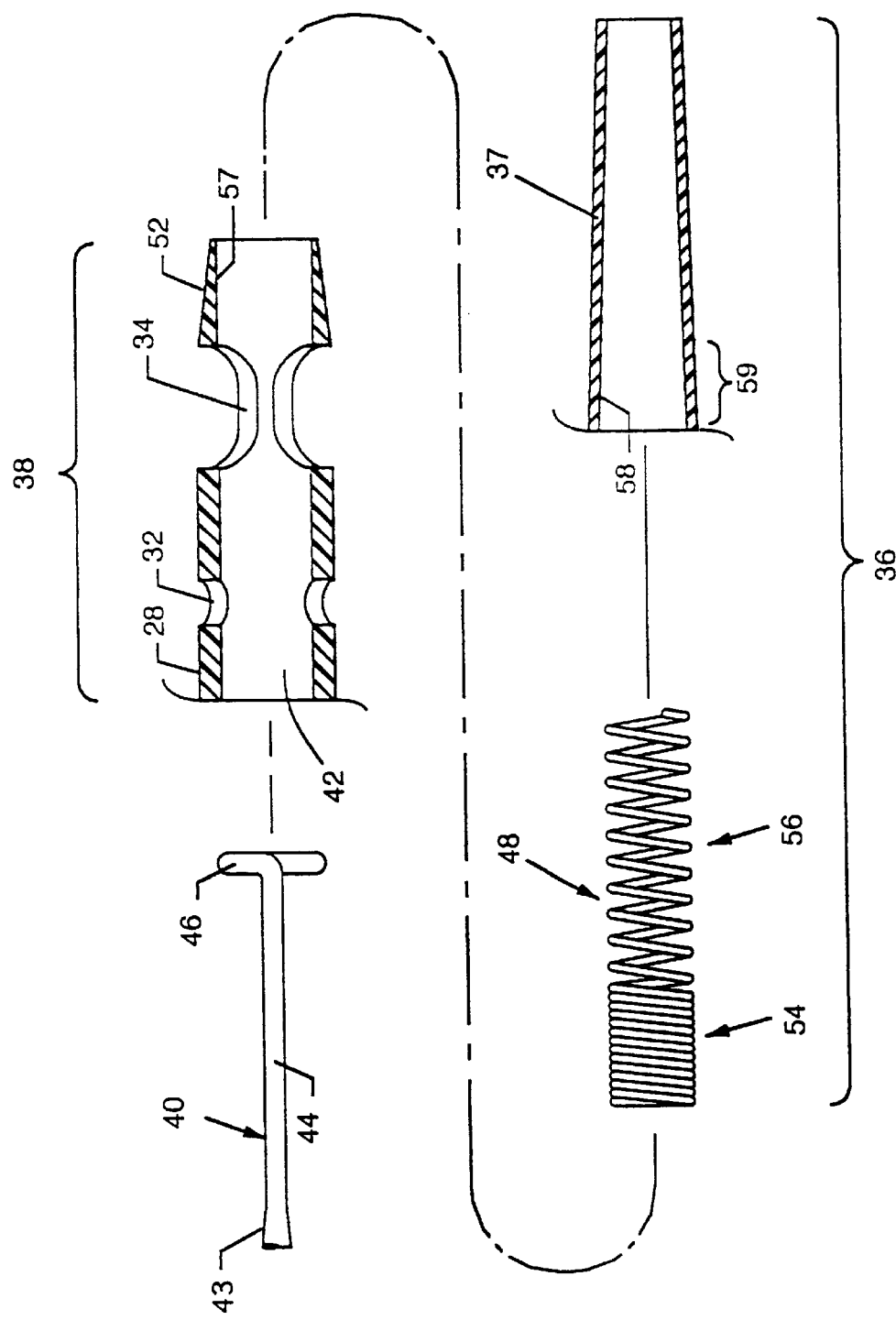
FIG. 2 illustrates an exploded view in cross section of the distal end of the cross stream thrombectomy catheter.
Figure 3:
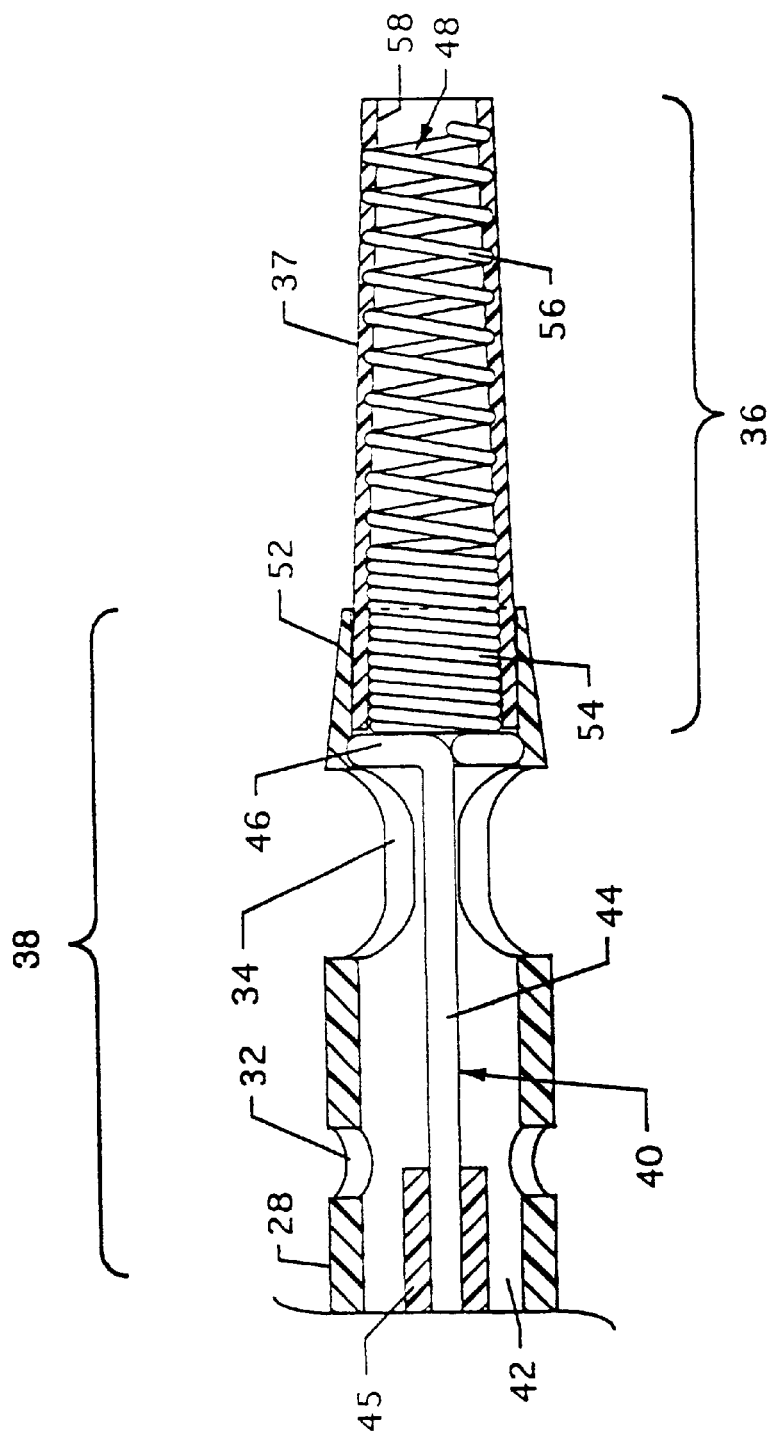
FIG. 3 illustrates an assembled view in cross section of the distal end of the cross stream thrombectomy catheter.

FIGS. 2 and 3 illustrate an exploded view and an assembled view in cross section of the distal end 38 and other distally located components of the cross stream thrombectomy catheter 10, respectively, where all numerals mentioned before correspond to those elements previously described. The primary two components of the cross stream thrombectomy catheter 10 are first and second tubular means, the first being a high pressure tubular means made of metal or high tensile strength polymer or composite material and shown in the form of a hypo-tube 44 formed into a jet body 40, and the second being in the form of an exhaust tubular means made of a flexible polymer and shown in the form of an exhaust tube 28 having a centrally located exhaust lumen 42. The jet body 40 is formed from a small hypo-tube 44 with a size range of 0.010 to 0.030 inch outer diameter. The distal portion of the hypo-tube 44 may be reduced to a small diameter as shown by reduction 43 (FIG. 2) to make the catheter more flexible by drawing the hypo-tube 44 through a die. The distal end of the hypo-tube 44 is then welded shut and the end formed into a toroidal loop jet emanator 46 or a jet emanator of other shape which will provide a surface in which proximally directed jet orifices 60a–60n (FIG. 4a), ranging from 0.001 to 0.010 inch in diameter, may be formed that will direct jetted saline or other body-compatible solution including mixtures of saline and medications or mixtures of saline and a contrast medium in a flow at or close to a path parallel to and in the opposite direction of the fluid flow in the interior of the hypo-tube 44 of the jet body 40. Alternatively, the jet body 40 may be of a short length and connected to a more flexible polymeric tube 45 (FIG. 3) in lieu of having a jet body 40 which extends proximally for the majority of the distance to the manifold 12. A radio-opaque marker coil 48 in the form of a stainless steel or platinum alloy coil, for example, may be adhered to the end of the jet body 40 and other components, as later described in detail.

The jet body 40, which has a smaller axial profile than that of the exhaust lumen 42, is inserted through and located within the exhaust lumen 42. The exhaust lumen 42 is central to the exhaust tube 28, which could also have multiple lumens, which has an outer diameter ranging from 0.030 to 0.150 inch, and which is also flexible and similar to the hypo-tube 44 in that it may be reduced to a smaller diameter to make the catheter more flexible by drawing through a die. The tapered and flexible tip assembly 36 includes a flexible plastic tapered tube 37 which encapsulates and surrounds the radio-opaque marker coil 48, which has a closely wound portion 54 and a loosely wound portion 56. Alternatively, the radio-opaque marker coil 48 can have uniform wind spacing, or can be omitted in favor of a polymeric tip.

A mechanical bond can be made between the distal tip of the jet body 40 at the junction of the toroidal loop jet emanator 46 and the exhaust lumen 42. For example, thermal and partial melting of the tapered distal tip 52 of the polymer exhaust tube 28 partially encapsulates the toroidal loop jet emanator 46 or other distal shape of the jet body 40. Thermal melting can also be incorporated to join the interior wall 57 of the exhaust tube 28 to the proximal area 59 of the tapered tube 37 whereby further heat transfer and melting can also encapsulate and join the closely wound portion 54 and the loosely wound portion 56 of the radio-opaque marker coil 48 to the interior wall 58 of the tapered tube 37. In the alternative, an adhesive can also be incorporated to join the toroidal loop jet emanator 46 to the interior of the exhaust tube 28 and to the proximal portion of the closely wound spring portion 54 and to the proximal area 59 of the tapered tube 37. Multiple inflow and outflow orifices can be formed anywhere as desired along the length of exhaust tube 28, either before or after the loading of the jet body 40, preferably in the distal portion, which as described below includes inflow and outflow orifices 34 and 32, respectively. Although the preferred embodiment of the catheter is made with multiple outflow and inflow orifices 32 and 34, a substantially equivalent catheter could be designed such that the catheter has only one extended orifice, but separate regions in that one orifice provide inflow and outflow of fluid. Preferably, the inflow and outflow orifices 34 and 32 are oval or round in shape, but they can be of other suitable geometric configuration or shape.

FIGS. 4a through 4g illustrate jet emanator means which may be utilized at the end of and which are located at the distal end of the jet body 40, each of which directs high velocity jet streams proximally along or near the longitudinal axis of the jet body 40 and the exhaust tube 28. Each jet emanator means comprises a tubular structure through which pressurized fluid flows creating high velocity fluid jets which emanate from one or more orifices in the tubular structure. The tubular structure can be of straight, curved, L-shaped, J-shaped, U-shaped, helical, toroidal or semi-toroidal shape, or can be a chamber such as a manifold, and may be formed of a single component, such as a metal hypo-tube, or of multiple components, such as multiple hypo-tubes, welded manifold components, or molded manifold components. The tubular structure forming the jet emanator means may be formed as a unitary part of the high pressure tubular means such as by forming a metal hypo-tube into a toroidal shape, or one of the other shapes mentioned above, with a single orifice or multiple orifices produced by drilling or cutting. The orifices can be round, slits, or other shapes so that fluid flowing therethrough forms one or more discrete high velocity fluid jets or merges into combination jets. Alternatively, the tubular structure forming the jet emanator means may be a separate structure having any one of the aforementioned shapes and orifice constructions which is attached to the distal end of the high pressure tubular means. In either event, the tubular structure forming the jet emanator means is in fluid communication with the high pressure tubular means. In each figure, highly pressurized fluid(s) first passes through a lumen 41 enroute to the variously shaped and configured distally located jet emanator means located at the end of the jet body 40.

FIG. 4a illustrates an isometric view of the toroidal loop jet emanator 46, one jet emanator means of which may be utilized at the end of and which is located at the distal end of the jet body 40, where all numerals mentioned before correspond to those elements previously described. Illustrated in particular are the plurality of proximally directed jet orifices 60a–60n located on the proximal surface of the toroidal loop jet emanator 46 which direct high velocity jet streams proximally, as shown by dashed lines, along or near the longitudinal axis of the jet body 40 and the exhaust tube 28. The toroidal loop jet emanator 46 includes a circular space 50 along the inner circumference to provide for and to accommodate alignment of and for passage along a guidewire, such as the guidewire 51 shown partially in FIG. 5. Multiple jet orifices 60a–60n located at points along the toroidal loop jet emanator 46 can advantageously direct high velocity jet streams on multiple sides of the guidewire 51 when it is positioned in the circular space 50 to avoid having guidewire 51 block inflow orifice(s) 34 or outflow orifice(s) 32 which could hamper the recirculation pattern, such as that shown in FIGS. 5 and 6.

Figure 4B:
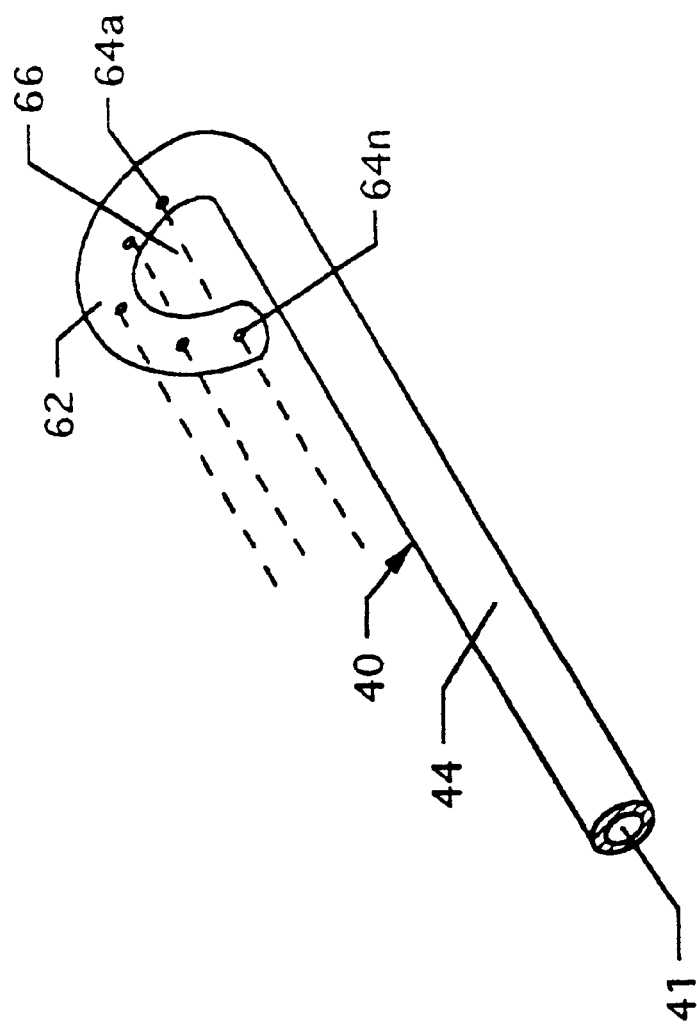
FIG. 4b illustrates an isometric view of a semi-toroidal loop jet emanator.

FIG. 4b illustrates an isometric view of a semi-toroidal loop jet emanator 62, another jet emanator means of which may be utilized at the end of and which is located at the distal end of the jet body 40, where all numerals mentioned before correspond to those elements previously described. Illustrated in particular are the plurality of proximally directed jet orifices 64a–64n located on the proximal surface of the semi-toroidal loop jet emanator 62 which direct high velocity jet streams proximally, as shown by dashed lines, along or near the longitudinal axis of the jet body 40 and the exhaust tube 28. The semi-toroidal loop jet emanator 62 includes a semi-circular space 66 along the inner circumference to provide for and to accommodate alignment of and for passage along a guidewire.

Figure 4C:
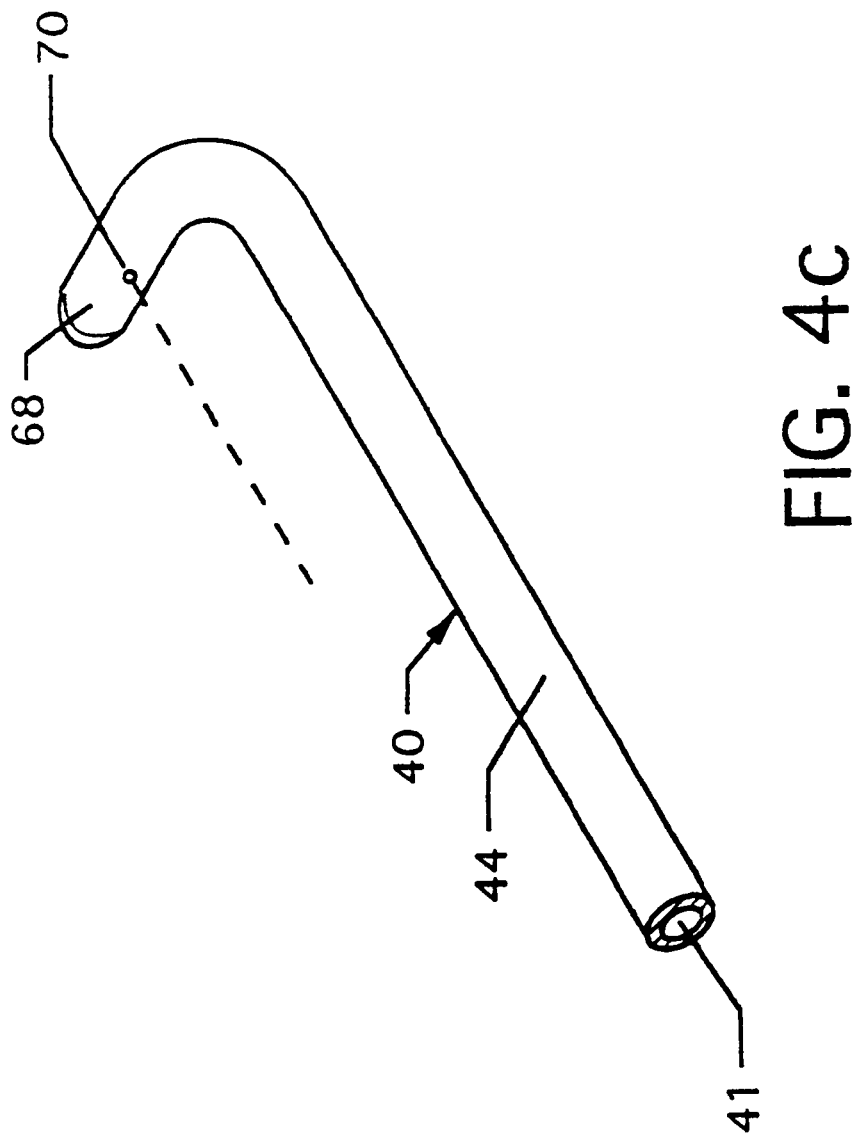
FIG. 4c illustrates an isometric view of an L-shaped jet emanator.

FIG. 4c illustrates an isometric view of an L-shaped jet emanator 68, another jet emanator means of which may be utilized at the end of and which is located at the distal end of the jet body 40, where all numerals mentioned before correspond to those elements previously described. Illustrated in particular is a proximally directed jet orifice 70 located on the proximal surface of the L-shaped jet emanator 68 which directs a high velocity jet stream proximally, as shown by a dashed line, along or near the longitudinal axis of the jet body 40 and the exhaust tube 28.

Figure 4D:
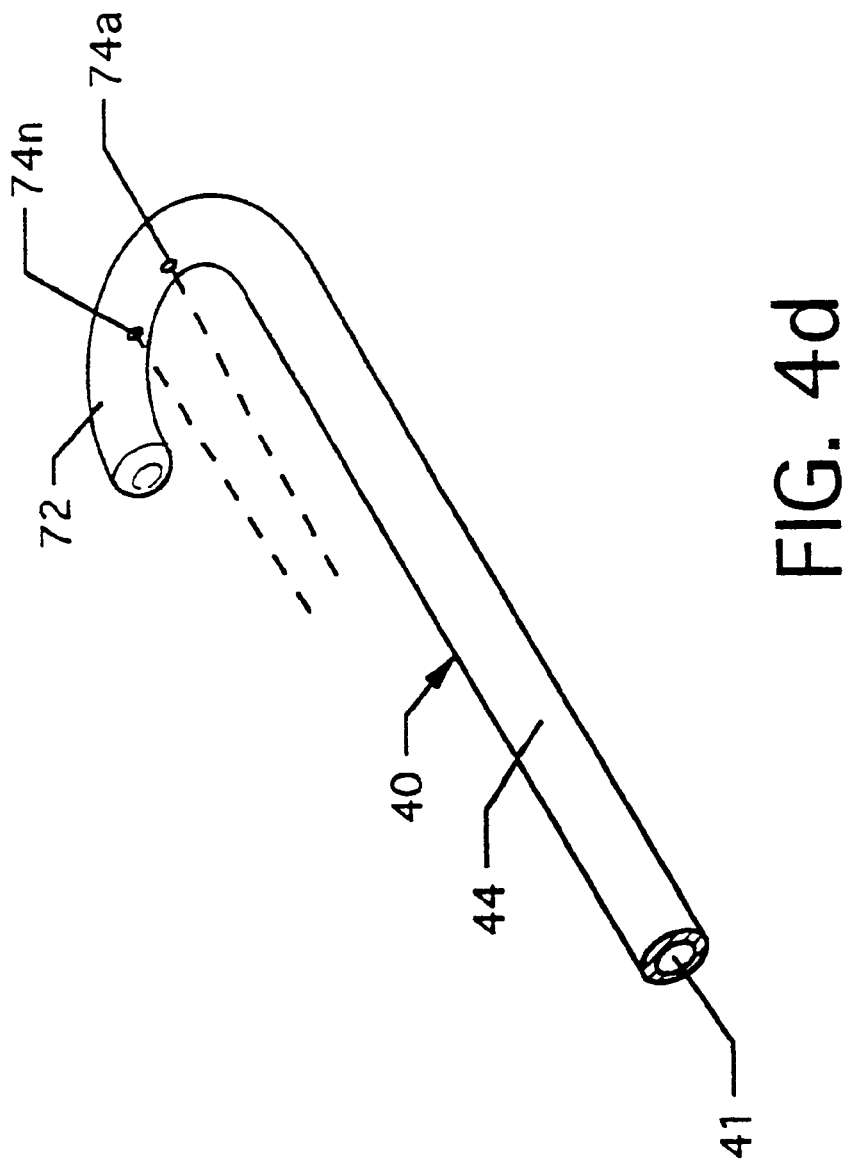
FIG. 4d illustrates an isometric view of a J-shaped jet emanator having jet orifices located on the J-shaped proximal facing surface.

FIG. 4d illustrates an isometric view of a J-shaped jet emanator 72 having jet orifices located on the J-shaped proximal facing curved surface, another jet emanator means of which may be utilized at the end of and which is located at the distal end of the jet body 40, where all numerals mentioned before correspond to those elements previously described. The J-shaped jet emanator 72 and the jet body 40 and hypo-tube 44 align in a common plane. Illustrated in particular is a plurality of proximally directed jet orifices 74a–74n located on the proximal curved surface of the J-shaped jet emanator 72 which direct high velocity jet streams proximally, as shown by dashed lines, along or near the longitudinal axis of the jet body 40 and the exhaust tube 28.

Figure 4E:
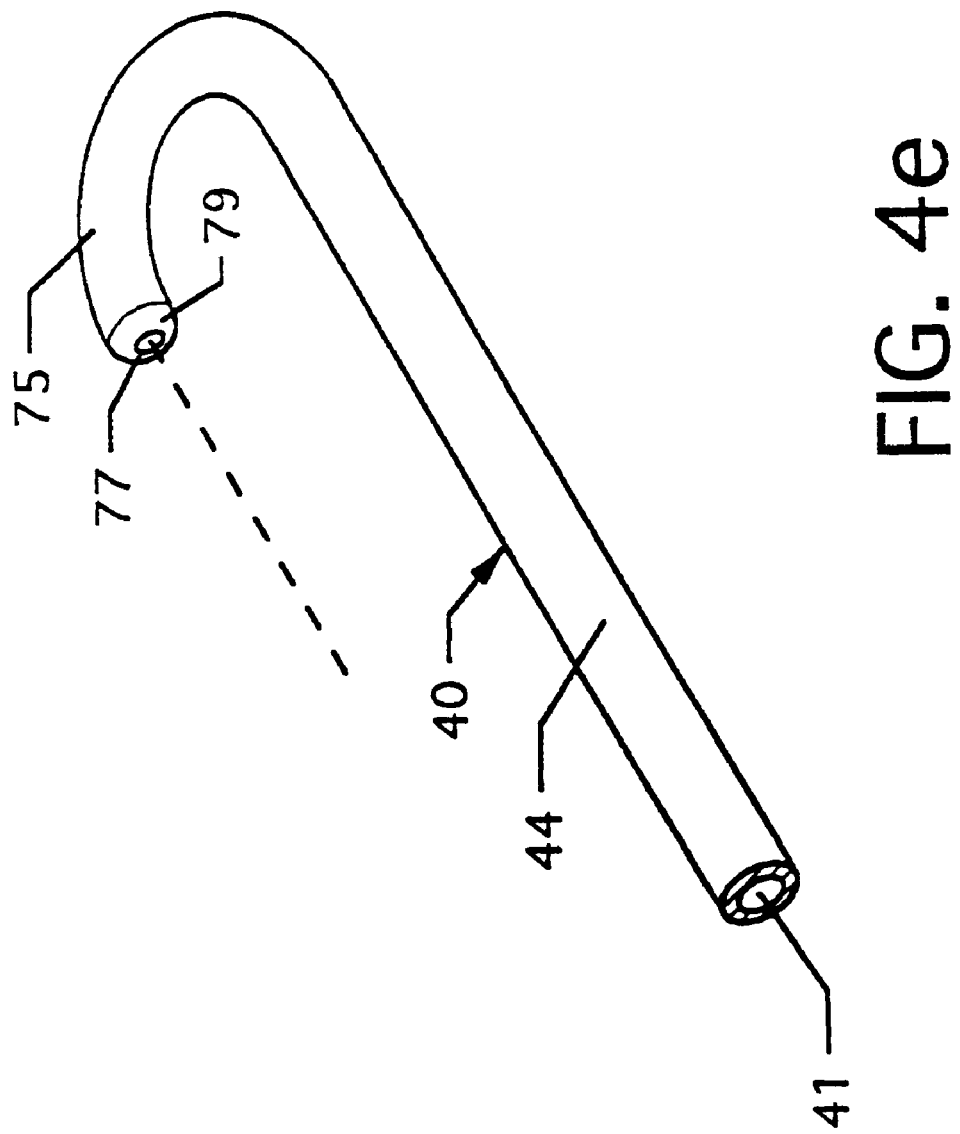
FIG. 4e illustrates an isometric view of a J-shaped jet emanator having a jet orifice located at the jet emanator extreme end.

FIG. 4e illustrates an isometric view of a J-shaped jet emanator 75 having a jet orifice located at the emanator end, being another jet emanator means of which may be utilized at the end of and which is located at the distal end of the jet body 40, where all numerals mentioned before correspond to those elements previously described. The J-shaped jet emanator 75 and the jet body 40 and hypo-tube 44 align in a common plane. Illustrated in particular is a proximally directed jet orifice 77 located at the extreme end 79 of the J-shaped jet emanator 75 which directs a high velocity jet stream proximally, as shown by a dashed line, along or near the longitudinal axis of the jet body 40 and the exhaust tube 28. The extreme end 79 preferably is first welded shut to form a dome or other suitably shaped structure which is drilled or bored to form the appropriately sized jet orifice 77.

Figure 4F:
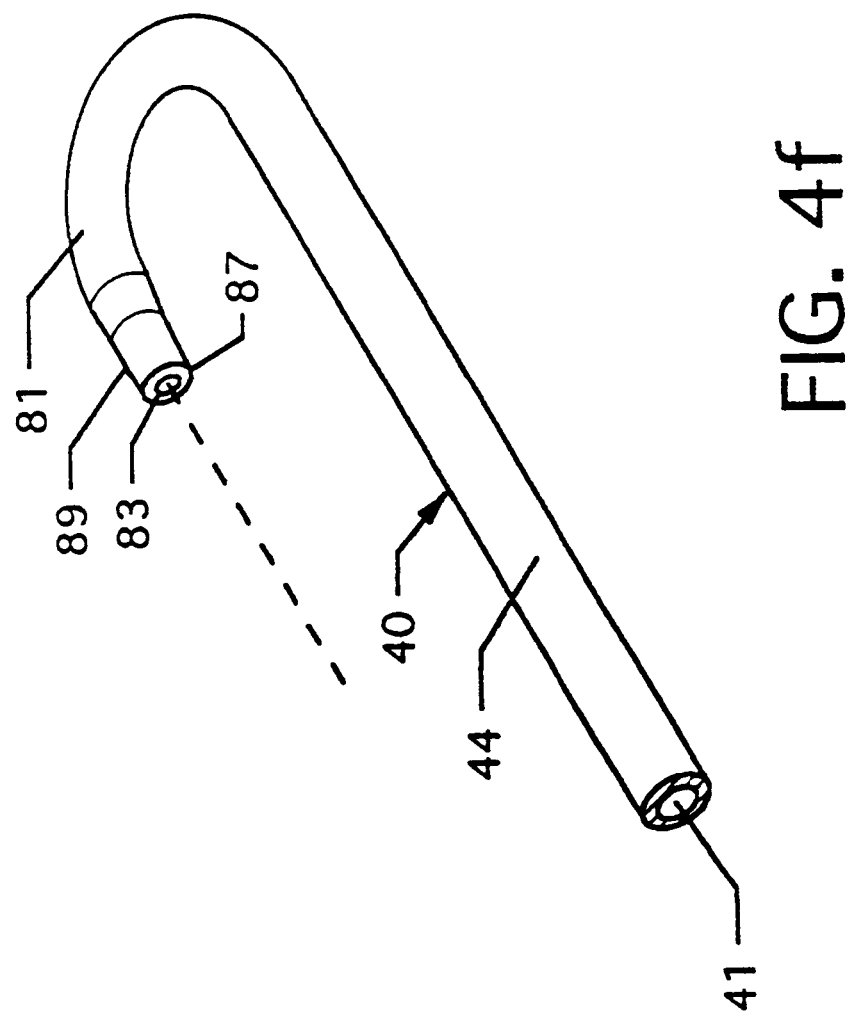
FIG. 4f illustrates an isometric view of a J-shaped jet emanator having a necked-down portion and co-located orifice.

FIG. 4f illustrates an isometric view of a J-shaped jet emanator 81 having a necked-down region and co-located orifice, another jet emanator means of which may be utilized at the end of and which is located at the distal end of the jet body 40, where all numerals mentioned before correspond to those elements previously described. The J-shaped jet emanator 81 and the jet body 40 and hypo-tube 44 and a necked-down portion 89 align in a common plane. Illustrated in particular is a proximally directed jet orifice 83 located at the extreme end 87 of the necked-down portion 89 of the J-shaped jet emanator 81 which directs a high velocity jet stream proximally, as shown by a dashed line, along or near the longitudinal axis of the jet body 40 and the exhaust tube 28. The necked-down portion 89 is appropriately drawn, formed and/or sized to produce an appropriately sized jet orifice 83.

Figure 4G:
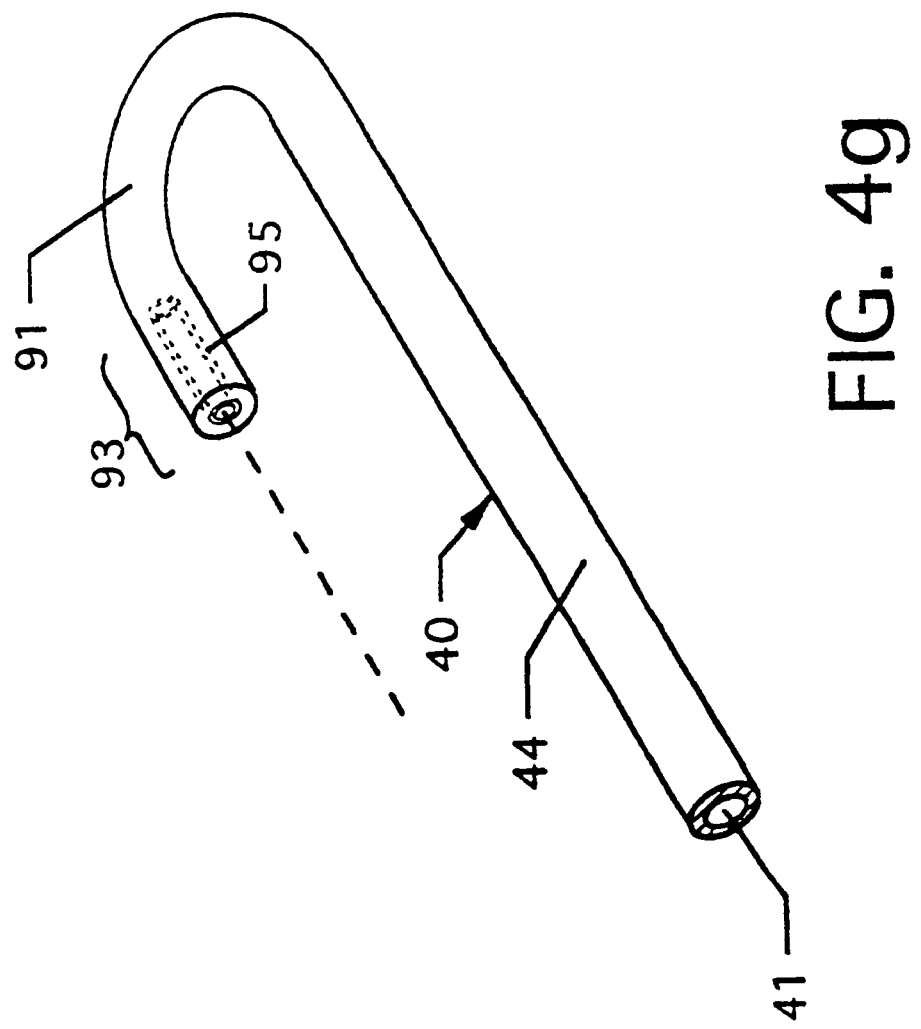
FIG. 4g illustrates an isometric view of a J-shaped jet emanator having an inserted tubular orifice member.

FIG. 4g illustrates an isometric view of a J-shaped jet emanator 91 having an inserted tubular orifice member, another jet emanator means of which may be utilized at the end of and which is located at the distal end of the jet body 40, where all numerals mentioned before correspond to those elements previously described. The J-shaped jet emanator 91 and the jet body 40 and hypo-tube 44 align in a common plane. The J-shaped jet emanator 91 includes a housing 93 which is part of and which extends proximally from the curved region of the J-shaped jet emanator 91. The housing 93 accommodates within an appropriately sized tubular orifice member 95 which directs a high velocity jet stream proximally, as shown by a dashed line, along or near the longitudinal axis of the jet body 40 and the exhaust tube 28.

MODE OF OPERATION

Figure 5:
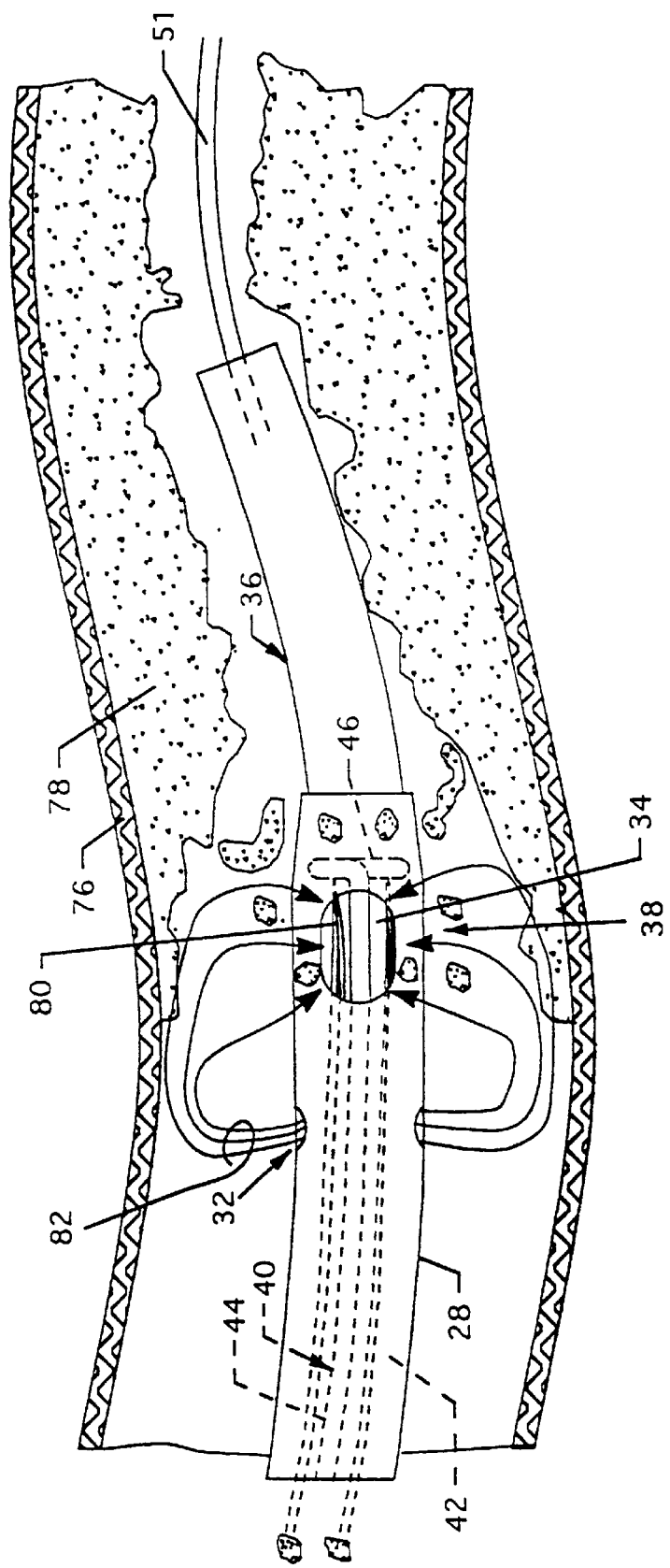
FIG. 5 illustrates a mode of operation view of the cross stream thrombectomy catheter positioned in a blood vessel, artery or the like at the site of a thrombotic deposit or lesion.

FIG. 5 illustrates in cross section a mode of operation view of the cross stream thrombectomy catheter 10 with particular attention to the distal end 38 of the exhaust tube 28 positioned in a blood vessel 76, artery or the like at the site of a thrombotic deposit or lesion 78. High velocity jets 80 of saline (or other suitable fluid) are shown being emitted in a proximal direction from the toroidal loop jet emanator 46. The semi-toroidal loop jet emanator 62 of FIG. 4b, L-shaped jet emanator 68 of FIG. 4c, the J-shaped jet emanator 72 of FIG. 4d, the J-shaped jet emanator 75 of FIG. 4e, the J-shaped jet emanator 81 of FIG. 4f, or the J-shaped emanator 91 of FIG. 4g can be incorporated at the distal portion of the jet body 40, as well as and as an alternative to the toroidal loop jet emanator 46 illustrated in this figure, to emanate or emit one or more high velocity jets 80 distally along or near the longitudinal axis of the jet body 40 and the exhaust tube 28. The saline fluid of jet(s) 80 passes outwardly through the outflow orifice(s) 32 in a radial direction creating cross stream jet(s) 82 (lower velocity jet(s)) directed outwardly toward the wall of the blood vessel 76 and are influenced by the low pressure at the inflow orifice(s) 34 to cause the cross stream jet(s) 82 to flow circumferentially and distally to impinge on, provide drag forces on, and break up thrombotic deposits or lesions 78 and to, by entrainment, urge and carry along the particles of thrombotic deposits or lesions 78 through the inflow orifice(s) 34, a relatively low pressure region, and into the exhaust lumen 42. The entrainment through the inflow orifice(s) 34 is based on entrainment by the high velocity jet(s) 80. The outflow is driven by internal pressure which is created by the high velocity jet(s) 80 and the fluid entrained through the inflow orifice(s) 34. The enhanced clot removal is because of the recirculation pattern established between inflow and outflow orifices 34 and 32, which creates a flow field that maximizes drag force on wall-adhered thrombus.

Figure 6:
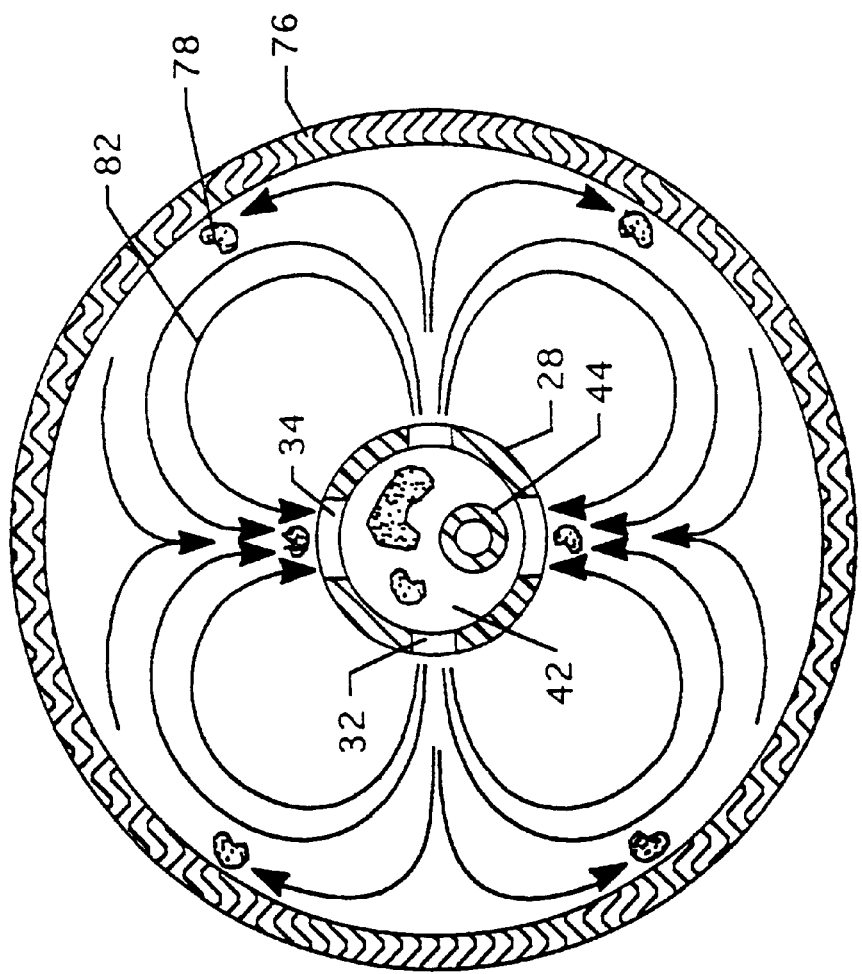
FIG. 6 illustrates the cross stream of saline jets from the outflow orifice(s) to the inflow orifice(s)

FIG. 6 illustrates in cross section the mode of operation view illustrating the cross stream jet(s) 82 (or stream(s)) and the recirculation pattern. For the purpose of clarity, the illustration shows the outflow orifice(s) 32 and the inflow orifice(s) 34 at the same station along the exhaust tube 28. Shown in particular is the flow of the cross stream jet(s) 82 which flow outwardly in radial fashion from the outflow orifice(s) 32 to impinge thrombotic deposits or lesions 78 and to urge and carry macerated thrombotic deposits or lesion particles 78 to the inflow orifice(s) 34 where the particles of thrombotic deposits or lesions 78 are entrained by the high velocity jet(s) 80 (not shown) and carried away through the exhaust lumen 42. Circumferential flow occurs along and substantially parallel to the inner boundary of the blood vessel 76 in a direction leading to the inflow orifice(s) 34.

MODE OF OPERATION

A manifold is attached to the tubular assembly on the proximal end to allow connection of the hypo-tube 44 of the jet body 40 to a 10 to 200 cc/min supply of saline (or other suitable fluid) at a back pressure in the range of approximately 150 psi to 50,000 psi, and to allow connection of exhaust lumen 42 to tubing attached to a collection system, preferably with exhaust regulation means involved to control the level of the exhaust. Suitable specific pressure ranges for the supply fluid can be approximately 150–500 psi, approximately 500–2,500 psi, or approximately 2,500–50,000 psi, depending on the particular situation involved.

The catheter is operated by injection with the high pressure saline supply through the threaded high pressure connection 11. The saline flows through the jet body 40 and into the jet emanator means wherein, depending on the supply pressure, it exists in pressure ranges of approximately 50–350 psi, 350–850 psi, or 850–35,000 psi. The saline exits the jet orifice(s) 60a–60n at a maximum instantaneous centerline velocity of approximately 2,000 to 30,000 cm/s, preferably 7,000 cm/s to 20,000 cm/s, and passes near at least one of the inflow orifice(s) 34 of the exhaust lumen 42. Since the catheter is operated in liquid media within the body, the saline jet(s) 80 behave as submerged jet(s) in that their momentum is transferred to the surrounding fluid, a phenomena known as entrainment. Due to the geometry of the catheter, the entrained fluid is brought into the inflow orifice(s) 34 in flow rates of 1 to 20 times that of the high velocity saline exiting the jet orifices 60a–60n.

Once entrained fluid has entered the inflow orifice(s) 34, the fluid will take the path of least resistance to exit the catheter. If the catheter were made with no outflow orifice(s) 32 and the exhaust lumen had no hydrodynamic resistance, all the entrained fluid would be exhausted out of the body through the exhaust lumen 42 and into the collection system. However, if there is significant amount of hydrodynamic resistance, either through pipe flow resistance in the exhaust lumen 42 or an exhaust regulation means, not all of the entrained fluid can be exhausted from the catheter. If there were no outflow orifice(s) 32 in the catheter, at least a portion of the inflow orifice(s) 34 will have fluid transported out of the catheter in order to maintain a mass balance of fluid in the catheter (all components of the catheter are incompressible or inelastic so that there is no accumulation of mass in the catheter).

The incorporation of outflow orifice(s) 32 in the catheter allows maintenance of the mass balance at the tip of the catheter without a requirement that a portion of the inflow orifice(s) 34 will have fluid transported out of the catheter. The benefit of removing the two-directional flow through the inflow orifice(s) 34 is that friction between the entrained fluid and fluid that is being transported out of the catheter has been eliminated. Thus, both of these flows will be increased by having the outflow orifice(s) 32 incorporated into the catheter to act to greatly enhance the thrombectomy effect of the catheter on organized mural thrombus.

Figure 7:
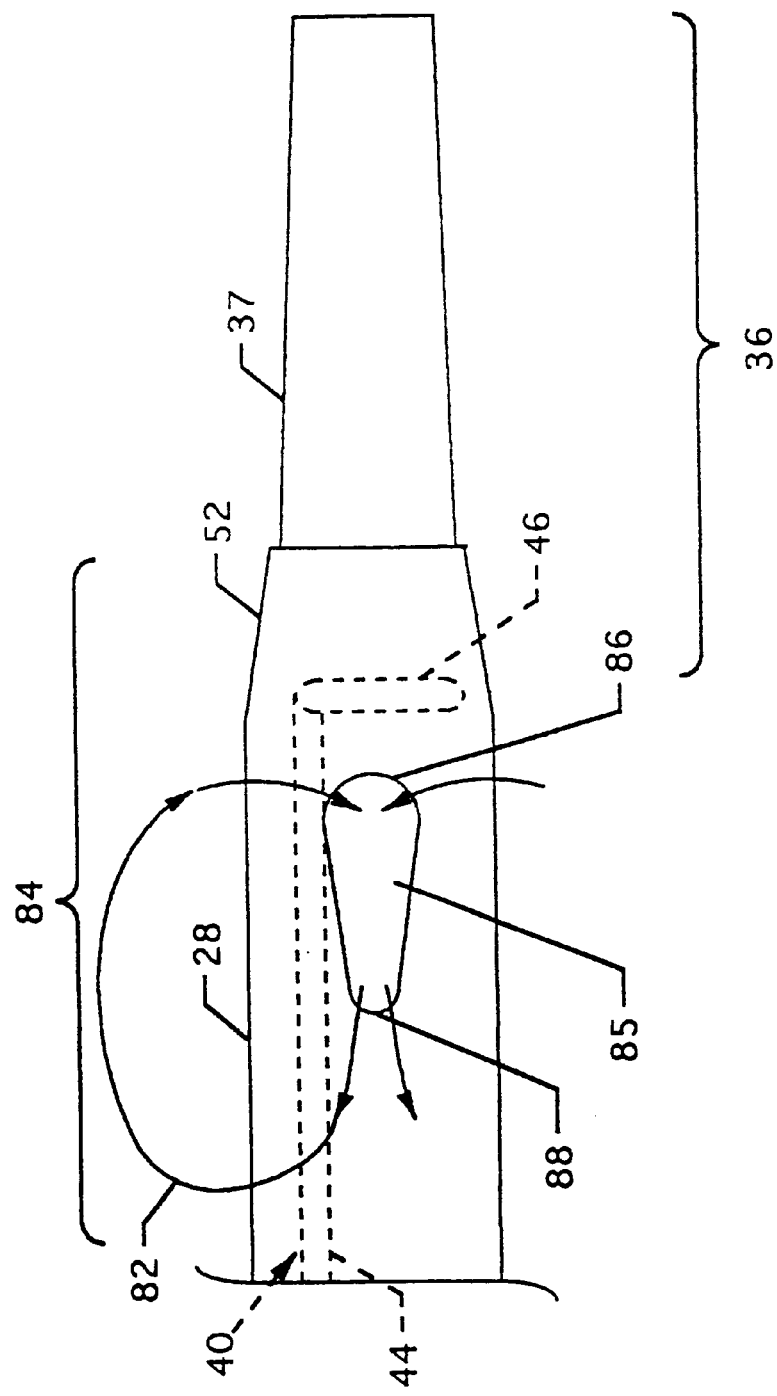
FIG. 7, a first alternative embodiment, illustrates a side view showing the distal end of an exhaust tube having a single-opening dual-function orifice.
Figure 8:
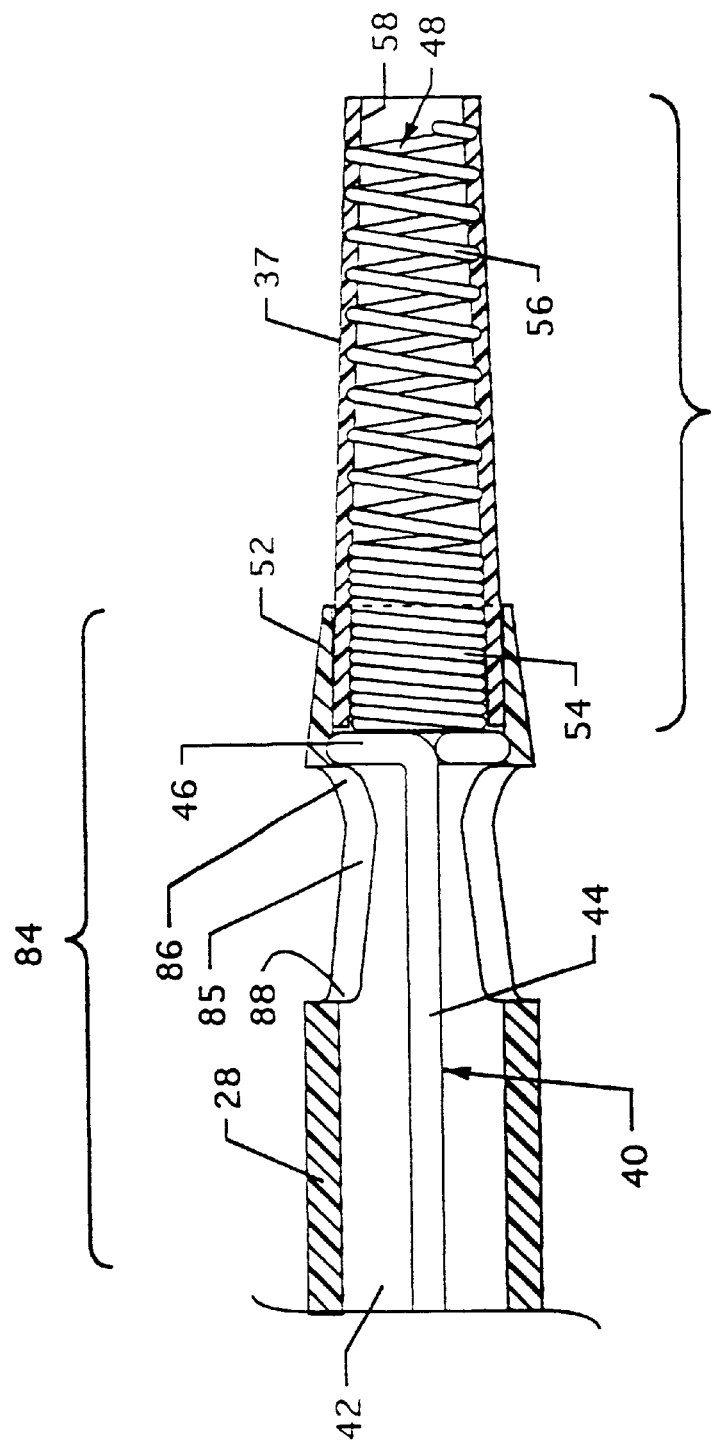
FIG. 8 illustrates a cross section view of the first alternative embodiment showing the distal end of the exhaust tube.

FIGS. 7 and 8 illustrate a side view and a cross section view, respectively, of a first alternative embodiment showing distal end 84 of the exhaust tube 28 which can be incorporated into use with the first embodiment of and for use with the majority of the components of the cross stream thrombectomy catheter previously described, where all numerals mentioned before correspond to those elements previously described. Although the preferred embodiment of the catheter includes multiple outflow and inflow orifices 32 and 34, a substantially equivalent catheter having one or more single opening dual function orifices 85 can be provided, each orifice 85 having separate regions such that one single opening orifice provides for inflow and outflow of fluid. Preferably, the orifice 85 is an elongated shape, but can be of other suitable geometric configuration or shape. FIG. 7 illustrates an elongated and tapered orifice 85 having at one end a semi-circular distally located radiused inflow end 86 corresponding to the inflow orifice 34 and a semi-circular proximally located relatively smaller radiused outflow end 88 corresponding to the outflow orifice 32 opposing the radiused inflow end 86. A cross stream thrombectomy catheter incorporating the distal end 84 of the exhaust tube 28 operates according to the teachings of the invention with the benefit of simpler and more easily accomplished construction which combines the inflow and outflow orifices into a single opening orifice. Although toroidal loop jet emanator 46 is shown in the embodiment, other jet emanators such the semi-toroidal loop jet emanator 62 of FIG. 4b, the L-shaped jet emanator 68 of FIG. 4c, the J-shaped jet emanator 72 of FIG. 4d, the J-shaped jet emanator 75 of FIG. 4e, the J-shaped jet emanator 81 of FIG. 4f, or the J-shaped jet emanator 91 of FIG. 4g, or other such suitable jet emanator or device can be incorporated into use with this embodiment of the present invention. Flow of the cross stream jet(s) 82 is illustrated in FIG. 7.

FIGS. 9 through 17 illustrate second, third and fourth alternative embodiments of distal ends of the exhaust tube 28 where the inflow orifices are located at the extreme end of the exhaust lumen 42 of the exhaust tube 28 as an alternative to inflow orifice placement on the sidewall of the exhaust tube 28 as previously described, and where use of the tapered and flexible tip assembly 36 is not required. The distal ends are assigned different designator number references in allowance for differently located inflow or outflow orifices or other variances or combinations thereof at or near the distal ends.

Figure 9:
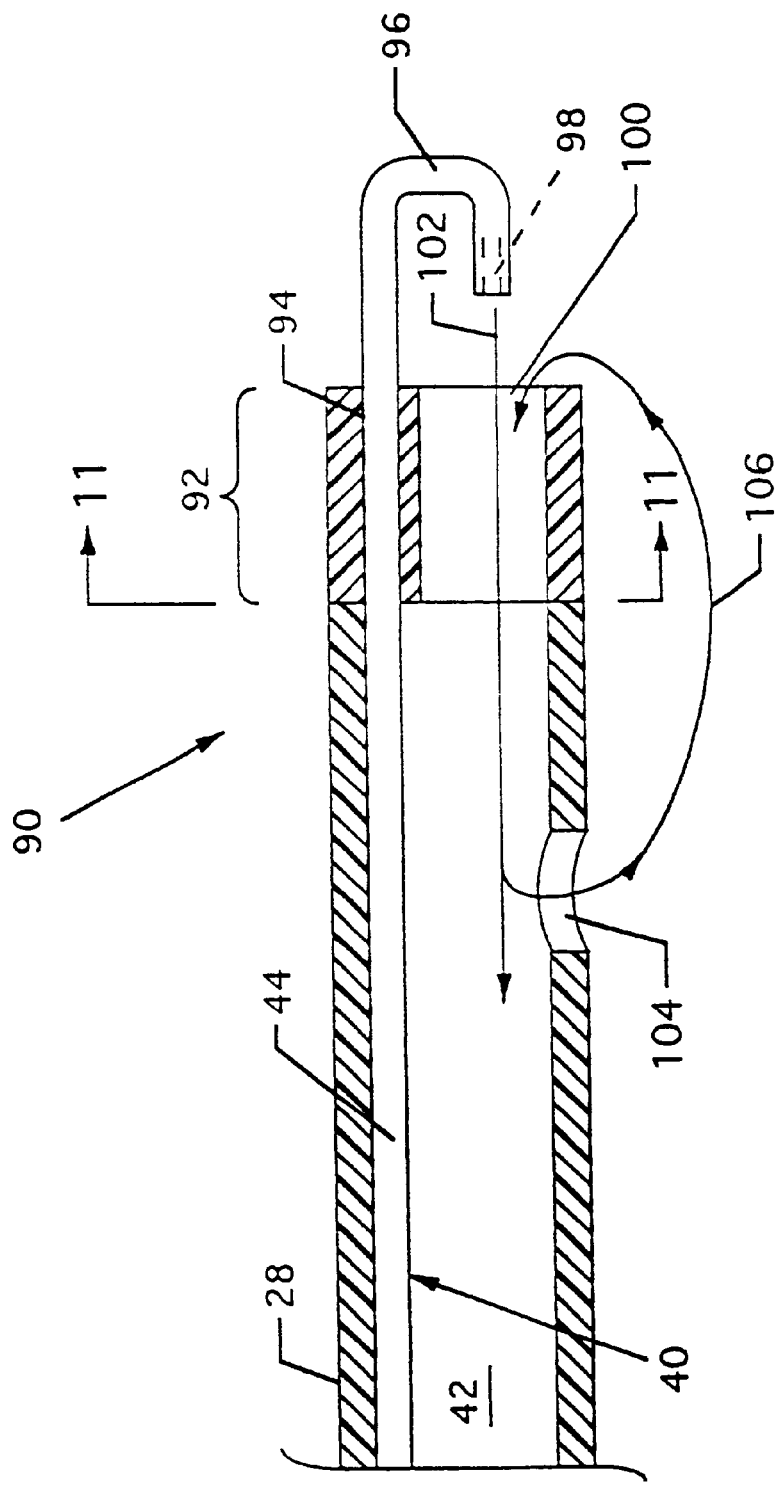
FIG. 9, a second alternative embodiment, illustrates a cross section view showing the distal end of an exhaust tube having a tip with a proximally facing planar surface and also showing a single-orifice U-shaped jet emanator aligned with an inflow orifice located at the end of the exhaust tube.
Figure 10:
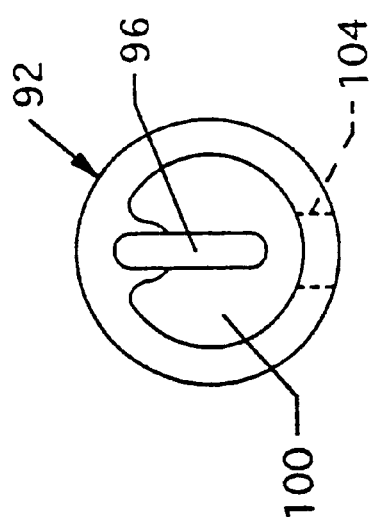
FIG. 10 illustrates an end view of the second alternative embodiment shown in FIG. 9.

FIGS. 9 and 10, illustrate a cross section view and an end view, respectively, of a second alternative embodiment showing distal end 90 of the exhaust tube 28 which can be incorporated into use with the manifold 12, the jet body 40 and the exhaust tube 28 with the exception of the tapered and flexible tip assembly 36 of the first embodiment and is intended for use with the majority of the components of the cross stream thrombectomy catheter previously described, where all numerals mentioned before correspond to those elements previously described. A tip 92 is located at or near the distal end of the jet body 40 and at the distal end 90 of the exhaust tube 28. The tip 92, which can be of metallic, polymeric or other suitable material, aligns and suitably secures to the distal end 90 of the exhaust tube 28. The tip 92 includes a bore 94 which supports the jet body 40. The jet body 40 extends distally beyond the bore 94 of the tip 92 and forms a U-shaped jet emanator 96 having a single centrally located jet orifice 98, which is the end of the lumen 41 of the extended jet body 40 making up the U-shaped jet emanator 96. The jet orifice 98 of the U-shaped jet emanator 96 is directed at an inflow orifice 100 aligned longitudinally and located in the tip 92. A high velocity jet 102 of saline is emitted in a proximal direction from the jet orifice 98 and through the inflow orifice 100. Fluid is entrained by the high velocity jet 102 and is thereby drawn through the inflow orifice 100 and driven into the exhaust lumen 42 and mixes with saline from the high velocity jet 102. Part of this entrained fluid mixed with the saline from the high velocity jet 102 passes outwardly through the outflow orifice 104 in a radial direction creating a cross stream jet 106 (lower velocity jet) directed outwardly toward the wall of a blood vessel and is influenced by the low pressure at the inflow orifice 100 to cause the cross stream jet 106 to flow circumferentially and distally to impinge on, provide drag forces on, and break up thrombotic deposits or lesions and to, by entrainment, urge and carry along the thrombotic deposits or lesions through the inflow orifice 100, a relatively low pressure region, and into the exhaust lumen 42. The flow of fluid and thrombotic deposits through the inflow orifice 100 is based on entrainment by the high velocity jet 102. The outflow through outflow orifice 104 is driven by internal pressure which is created by the high velocity jet 102 and the fluid entrained through the inflow orifice 100. The enhanced clot removal is because of the recirculation pattern established between inflow and outflow orifices 100 and 104, which creates a flow field that maximizes drag force on wall-adhered thrombus. Although a U-shaped jet emanator 96 is shown in the embodiment, other jet emanators such as the semi-toroidal loop jet emanator 62 of FIG. 4b, the L-shaped jet emanator 68 of FIG. 4c, the J-shaped jet emanator 72 of FIG. 4d, the J-shaped jet emanator 75 of FIG. 4e, the J-shaped jet emanator 81 of FIG. 4f, or the J-shaped jet emanator 91 of FIG. 4g, or other such suitable jet emanator or device can be incorporated into use with this embodiment of the present invention.

Figure 11:
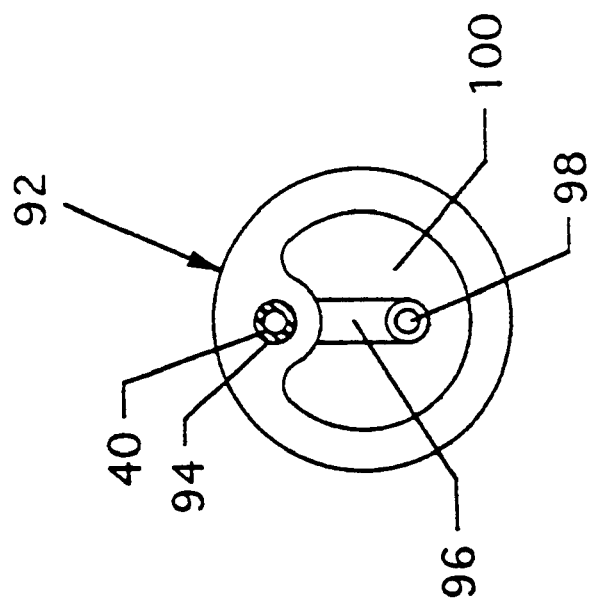
FIG. 11 illustrates a view of the tip at the distal end of the exhaust tube along line 11—11 of FIG. 9.

FIG. 11 illustrates a view of the tip 92 along line 11—11 of FIG. 9, where all numerals correspond to those elements previously described.

Figure 12:
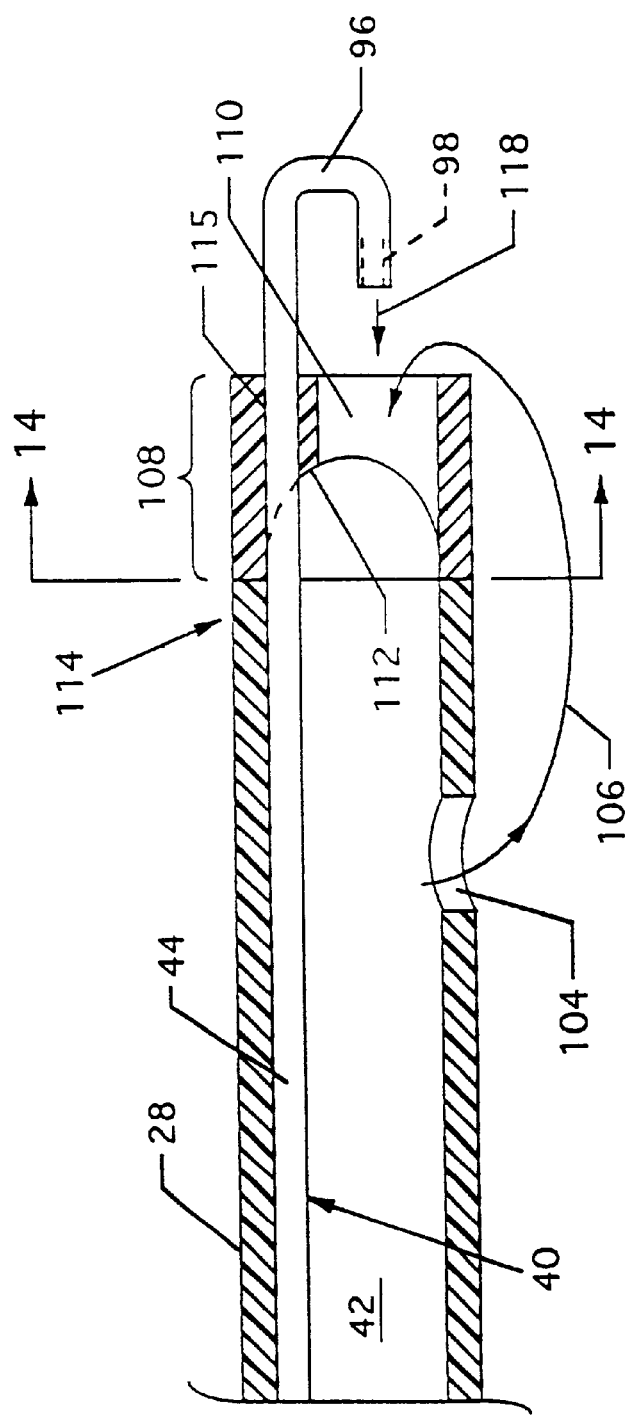
FIG. 12, a third alternative embodiment, illustrates a cross section view showing the distal end of an exhaust tube having a tip with a proximally facing curved surface and also showing a single-orifice U-shaped jet emanator aligned with an inflow orifice located at the end of the exhaust tube.
Figure 13:
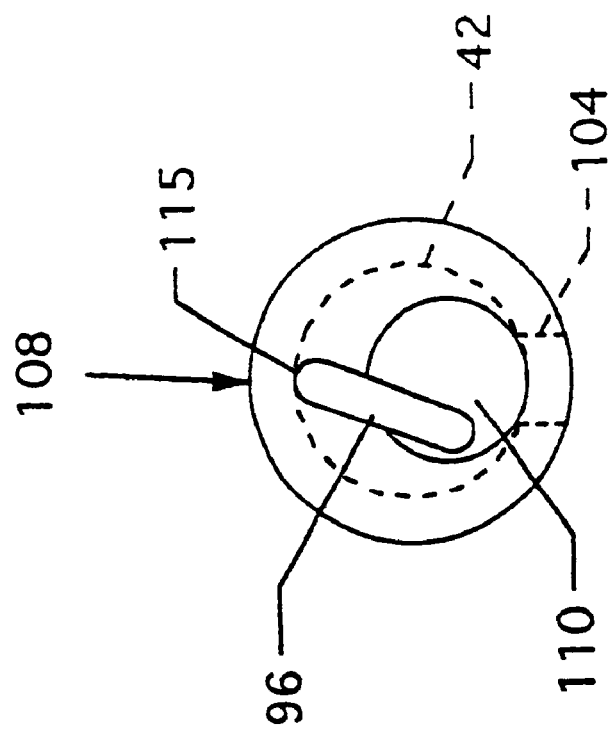
FIG. 13 illustrates an end view of the third alternative embodiment shown in FIG. 12.

FIGS. 12 and 13 illustrate a cross section view and an end view, respectively, of a third alternative embodiment which operates according to the teachings of the invention, and more specifically, according to the teachings of FIGS. 9, 10 and 11 and which incorporates many of the components shown in FIGS. 9, 10 and 11. FIGS. 12 and 13 illustrate a tip 108 having similarities to tip 92 of FIG. 9, but including an inwardly or proximally facing curved surface 112. The curved surface 112 assists and promotes alignment of a guidewire through an inflow orifice 110 of the tip 108. The distal end 114 of the exhaust tube 28 including the tip 108 can be incorporated into use with the manifold 12, the jet body 40 and the exhaust tube 28 with the exception of the tapered and flexible tip assembly 36 of the first embodiment and is intended for use with the majority of the components of the cross stream thrombectomy catheter previously described, where all numerals mentioned before correspond to those elements previously described. The tip 108 is located at or near the distal end of the jet body 40 and at the distal end 114 of the exhaust tube 28. The tip 108, which can be of metallic, polymeric or other suitable material, aligns and suitably secures to the distal end 114 of the exhaust tube 28. The tip 108 includes a bore 115 which supports the jet body 40. As previously described, the jet body 40 extends distally beyond the bore 115 of the tip 108 to form the U-shaped jet emanator 96 having a single centrally located jet orifice 98 which is the end of the lumen 41 of the extended jet body 40 making up the U-shaped jet emanator 96. The jet orifice 98 of the U-shaped jet emanator 96 is directed at an inflow orifice 110 aligned longitudinally and located in the tip 108. A high velocity jet 118 of saline is emitted in a proximal direction from the jet orifice 98 and through the inflow orifice 110 to operate in a manner and fashion such as described for FIGS. 9, 10 and 11. Although U-shaped jet emanator 96 is shown in the embodiment, other jet emanators such as the toroidal loop jet emanator 46 of FIG. 4a, the semi-toroidal loop jet emanator 62 of FIG. 4b, the L-shaped jet emanator 68 of FIG. 4c, the J-shaped jet emanator 72 of FIG. 4d, the J-shaped jet emanator 75 of FIG. 4e, the J-shaped jet emanator 81 of FIG. 4f, the J-shaped jet emanator 91 of FIG. 4g, or other such suitable jet emanator or device can be incorporated into use with this embodiment of the present invention.

Figure 14:
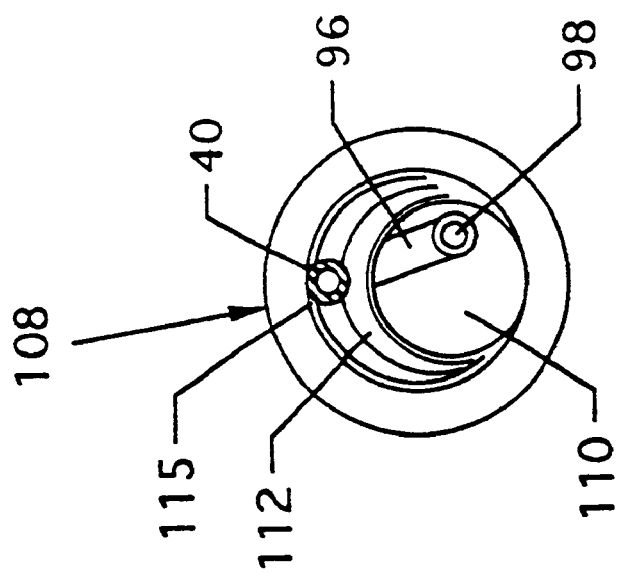
FIG. 14 illustrates a view of the tip at the distal end of the exhaust tube along line 14—14 of FIG. 12.

FIG. 14 illustrates a view of the tip 108 along line 14—14 of FIG. 12, where all numerals correspond to those elements previously described.

Figure 15:
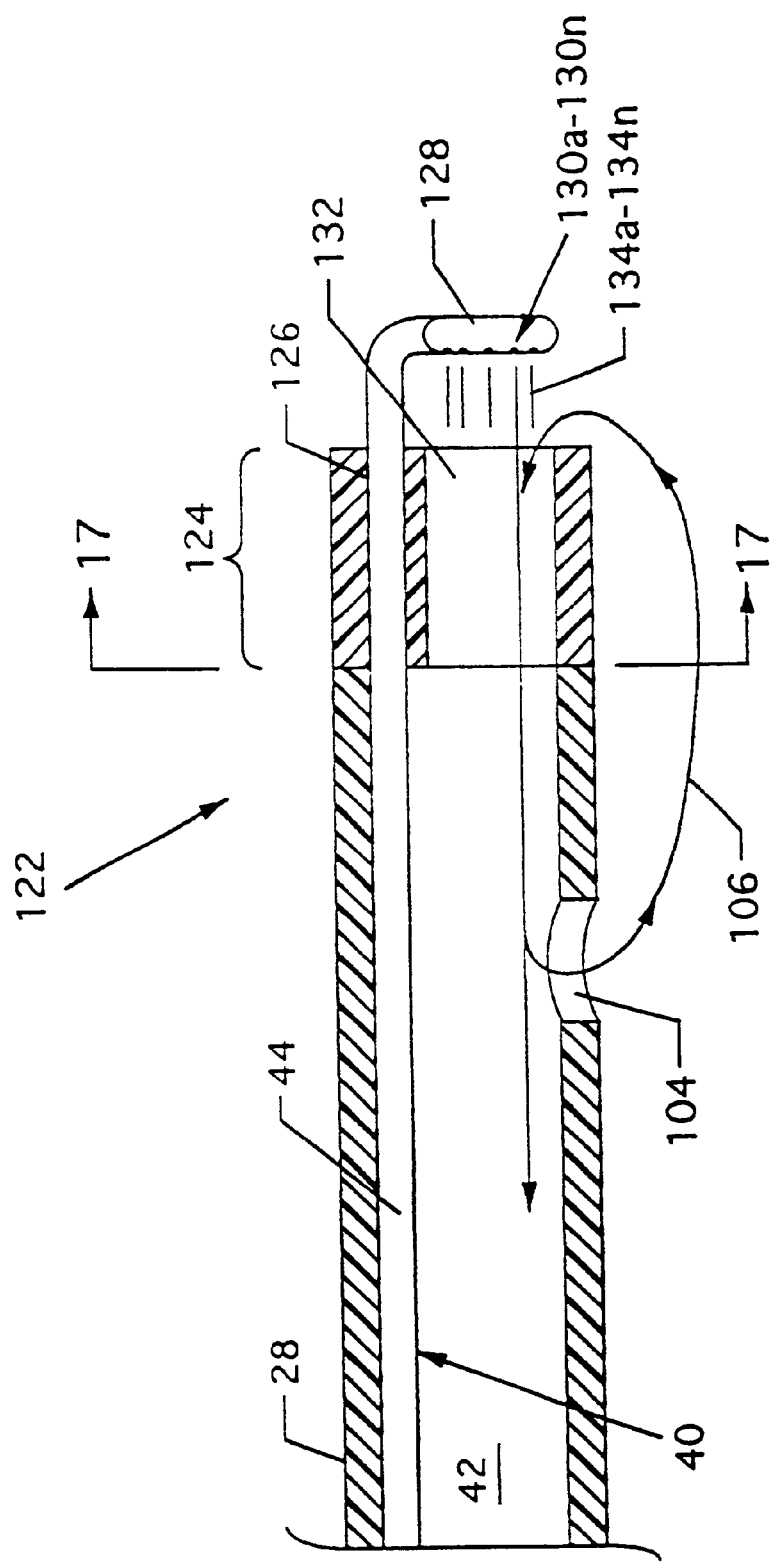
FIG. 15, a fourth alternative embodiment, illustrates a cross section view showing the distal end of an exhaust tube and showing a toroidal loop jet emanator aligned to an inflow orifice located at the end of the exhaust tube.
Figure 16:
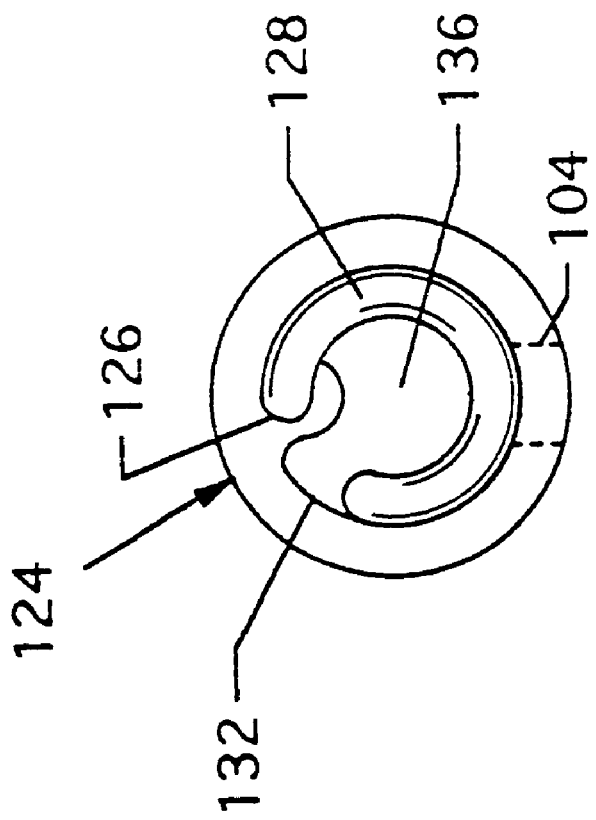
FIG. 16 illustrates an end view of the fourth alternative embodiment shown in FIG. 15.

FIGS. 15 and 16 illustrate a cross section view and an end view, respectively, of a fourth alternative embodiment showing distal end 122 of the exhaust tube 28 which can be incorporated into use with the manifold 12, the jet body 40 and the exhaust tube 28 with the exception of the tapered and flexible tip assembly 36 of the first embodiment and is intended for use with the majority of the components of the cross stream thrombectomy catheter previously described, where all numerals mentioned before correspond to those elements previously described. A tip 124 is located at or near the distal end of the jet body 40 and at the distal end 122 of the exhaust tube 28. The tip 124, which can be of metallic, polymeric or other suitable material, aligns and suitably secures to the distal end 122 of the exhaust tube 28. The tip 124 includes a bore 126 which supports the jet body 40. The jet body 40 extends distally beyond the bore 126 of the tip 124 and forms a toroidal loop jet emanator 128 having a plurality of proximally directed jet orifices 130a–130n. The jet orifices 130a–130n of the toroidal loop jet emanator 128 are directed at an inflow orifice 132 aligned longitudinally and located in the tip 124. The high velocity jets 134a–134n of saline are emitted in a proximal direction from the jet orifices 130a–130n and through the inflow orifice 132. Fluid, such as blood and thrombotic debris which may be near the tip 124, is entrained by the high velocity jets 134a–134n and is thereby drawn through inflow orifice 132 and acts in a manner and fashion such as described for FIGS. 9, 10 and 11, such that cross stream jets 106 and recirculation pattern between the outflow orifice 104 and the inflow orifice 132 synergistically enhances thrombus removal.

Figure 17:
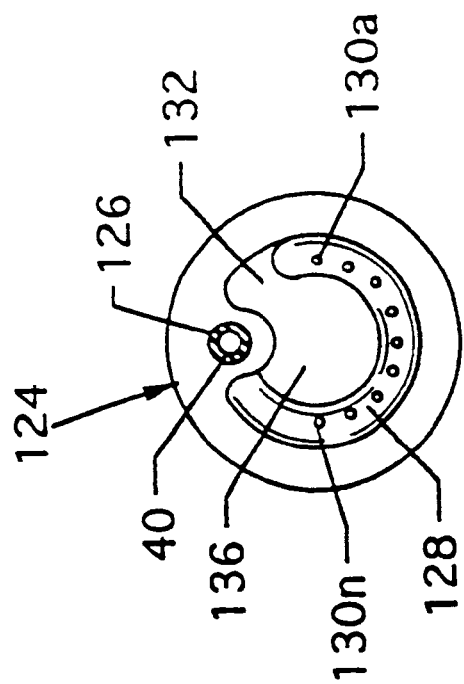
FIG. 17 illustrates a view of the tip at the distal end of the exhaust tube along line 17—17 of FIG. 15.

FIG. 17 illustrates a view of the tip 124 along line 17—17 of FIG. 15, where all numerals mentioned before correspond to those elements previously described. A circular space 136 along the inner circumference of the toroidal loop jet emanator 128 is provided to accommodate alignment and passage along a guidewire.

Figure 18:
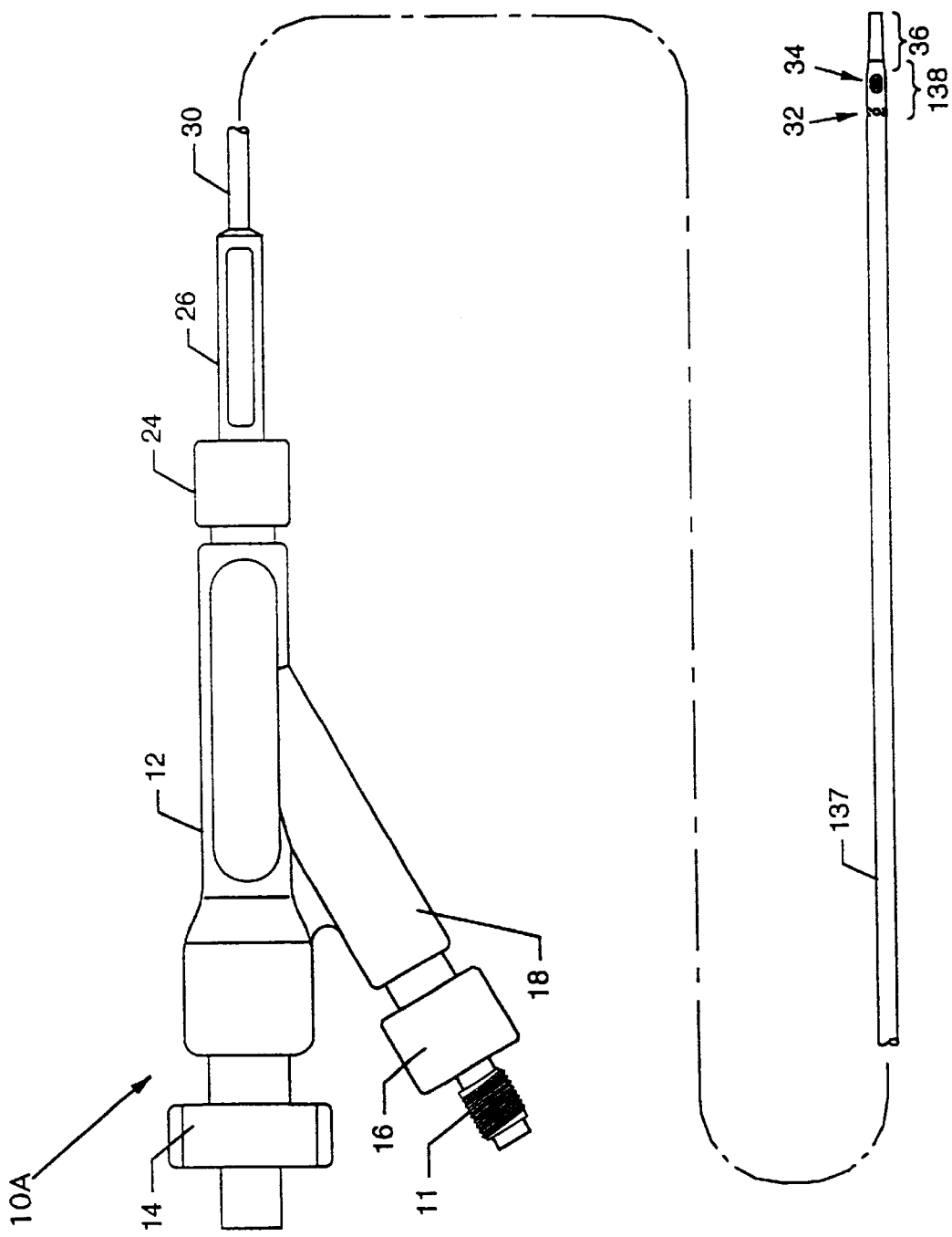
FIG. 18, a fifth alternative embodiment, illustrates a side view of an elongated device in the form of another cross stream thrombectomy catheter similar to that of FIG. 1, but without exhaust provision; and, FIG. 19 is a cross section view of the distal end of the cross stream thrombectomy catheter of FIG. 18.

FIG. 18, a fifth alternative embodiment, illustrates a side view of a cross stream thrombectomy catheter 10A which is similar to the cross stream thrombectomy catheter 10 of FIG. 1B but without exhaust provision, and therefore does not include the manifold branch 22 and Luer connection 20 which extend from manifold branch 18. Also, in this fifth alternative embodiment the toroidal loop jet emanator of the FIG. 1B embodiment is not employed, and since no exhaust provision is present, the second tubular means characterized by the exhaust tubular means in the form of the exhaust tube 28 of the FIG. 1B embodiment is characterized by other tubular means in the form of a tube 137 which is similar to the exhaust tube 28 of the FIG. 1B embodiment but which has a distal end 138 of different construction from that of the distal end 38 of the embodiment of FIG. 1B. Devices of the fifth alternative embodiment operate and function similarly to those of the FIG. 1B embodiment in that a recirculation pattern from outflow orifices 34 to inflow orifices 32 synergistically enhance clot breakup; however, this embodiment does not provide for removal of the thrombus debris through the catheter itself. If desired, thrombus debris can be removed from the body by separate means, such as a separate catheter or by chemical methods. In many cases, such thrombus debris removal would not be necessary since the enhanced clot breakup action of the device produces small debris which can be left in the body.

Figure 19:
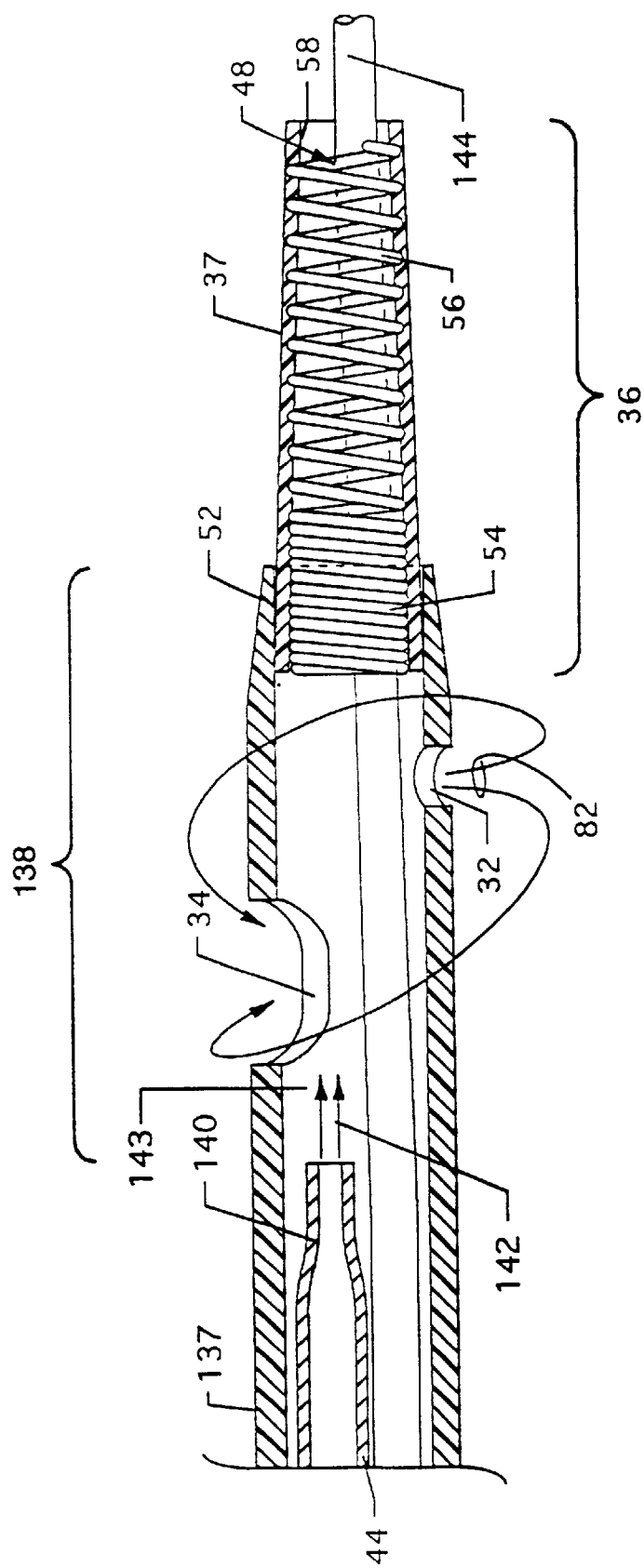

FIG. 19 depicts a cross section view of the distal end 138 of the tube 137. All numerals appearing in FIGS. 18 and 19 which have been mentioned before correspond to those elements previously described. Preferably, hypo-tube 44 is formed into jet body 140 which directs a single high velocity jet 142 distally past inflow orifice 34. Alternatively, jet body 140 may be of a short length and connected to a more flexible polymeric tube similar to polymeric tube 45 of FIG. 3. Fluid, such as blood and thrombotic debris which may be near distal end 138, is entrained by the high velocity jet 142 and is thereby drawn through inflow orifice 34. The fluid mixes with saline from the high velocity jet 142, and thrombus is broken apart and pulverized by the high velocity jet 142. The fluid mixed with saline from high velocity jet 142 creates an internal pressure near outflow orifice 32, which creates cross stream jet(s) 82 and a recirculation pattern, as indicated, from outflow orifice 32 to inflow orifice 34. The recirculation pattern includes radial and circumferential flow vectors, and can include axial flow vectors as well. The recirculation pattern creates a flow field that maximizes force on wall-adhered thrombus or lesion. A guidewire 144 is shown passing through the tapered and flexible tip assembly 36 and through the tube lumen 143. This fifth alternative embodiment of the present invention is similar in many respects to the other embodiments, but does not provide for thrombus debris removal out of the body through the catheter. In this embodiment, the key features of inflow/outflow orifices and recirculation allow thrombus to be pulled into the high velocity jet(s) and to be broken up sufficiently so that they can pass downstream in the blood vessel without significant embolic complications. The recirculation can provide for repeated passage of thrombus fragments into the high velocity jets(s) so that maceration of the thrombus can occur. This embodiment may be particularly useful in treating venous thrombus or arteriovenous graft thrombosis, as examples, where moderately small thrombus fragment embolization is less likely to be of concern. In other situations, isolation means can be incorporated to prevent significant embolization. This embodiment has certain advantages over others, in that jet body 140 is simpler to fabricate, smaller in overall diameter, and less expensive than the more complex configurations, and the manifold 12 of FIG. 18 is simpler and less expensive than that shown in FIG. 1B. Also, since there is no requirement for removal of debris through the catheter, tube 137 of FIG. 18 can be a smaller diameter than exhaust tube 28 of FIG. 1B. The resulting device can then be a smaller diameter and less stiff, which offers advantages in allowing a smaller access for inserting the catheter into a patient and advancing it to the location of the thrombus. While the simple, single-jet jet body 140 is preferred in the fifth alternative embodiment, multiple jets and multiple inflow and outflow orifices can be used. For example, a jet body configuration similar to the semi-toroidal loop jet emanator 62 of FIG. 4b could be used, provided that multiple jet orifices direct fluid jets distally past one or more inflow orifices. Multiple outflow orifices could be used as well, positioned farther from the jet(s) than the inflow orifice(s), or combination inflow/outflow orifice(s) similar to orifice(s) 85 of FIGS. 7 and 8 could be utilized.

THROMBECTOMY CATHETER AND SYSTEM PARTS LIST 10 cross stream thrombectomy catheter
10A cross stream thrombectomy catheter
11 threaded high pressure connection
12 manifold
14 hemostasis unit
16 Luer fitting
18 manifold branch
20 Luer connection
22 manifold branch
24 Luer fitting
26 strain relief
28 exhaust tube
30 proximal end
32 outflow orifice
34 inflow orifice
36 tapered and flexible tip assembly
37 tapered tube
38 distal end
40 jet body
41 lumen
42 exhaust lumen
43 reduction
44 hypo-tube
45 polymeric tube
46 toroidal loop jet emanator
48 marker coil
50 circular space
51 guidewire
52 distal tip (of exhaust tube)
54 closely wound portion
56 loosely wound portion
57 interior wall
58 interior wall
59 proximal area
60a–n jet orifices
62 semi-toroidal loop jet emanator
64a–n jet orifices
66 semi-circular space
68 L-shaped jet emanator
70 jet orifice
72 J-shaped jet emanator
74a–n jet orifices
75 J-shaped jet emanator
76 blood vessel
77 jet orifice
78 thrombotic
79 extreme end
80 high velocity jets
81 J-shaped jet emanator
82 cross stream jets 83 jet orifice
84 distal end
85 orifice
86 inflow end
87 extreme end
88 outflow end
89 necked-down portion
90 distal end
91 J-shaped jet emanator
92 tip
93 housing
94 bore
95 orifice member
96 U-shaped jet emanator
98 jet orifice deposit or lesion
100 inflow orifice
102 high velocity jet
104 outflow orifice
106 cross stream jet
108 tip
110 inflow orifice
112 curved surface
114 distal end
115 bore
118 high velocity jet
122 distal end
124 tip
126 bore
128 toroidal loop jet emanator
130a–n jet orifices
132 inflow orifice
134a–n high velocity jets
136 circular space
137 tube
138 distal end
140 jet body
142 jet
143 lumen
144 guidewire Various modifications can be made to the present invention without departing from the apparent scope hereof.

It is claimed:

1. A method of macerating thrombus or other unwanted material in a body vessel or cavity, comprising the steps of:
   a. providing an elongated device having a first tube residing within and extending along the length of a second tube, said first tube having at its distal end jet emanator means for directing at least one high velocity fluid jet, inflow means for passage of entrained blood or other fluid from the body vessel into said second tube, outflow means for passage of fluid and entrained blood or other fluid from said second tube into the body vessel, said jet emanator means oriented so that at least one of said high velocity fluid jet(s) entrains and draws surrounding blood or other fluid from the body vessel or cavity through said inflow means and into said second tube, and said jet emanator means located with respect to said outflow means such that at least some fluid directed by said jet emanator means passes through said at least one outflow means;
   b. inserting said elongated device into a body vessel or cavity, and advancing said elongated device to a site of thrombus or other unwanted material in the body vessel or cavity;
   c. connecting said elongated device to a source of pressurized fluid so that fluid jet(s) emanate from said jet emanator means, entrains blood or other fluid which may contain thrombus or other unwanted material and draws the blood or other fluid into said second tube through said inflow means, and creates a pressurized region in said second tuba which drives fluid and entrained blood or other fluid which may contain thrombus or other unwanted material out of said second tube through said outflow means creating cross stream jet(s) of fluid and entrained blood or other fluid; and,
   d. using said elongated device to break apart thrombus or other unwanted material in the body vessel or cavity, where fluid forces from the cross stream jet(s) and a recirculation of fluid from said outflow means and back in through said inflow means and past said high velocity jet (s) macerates said thrombus or other unwanted material.

2. The method of claim 1, wherein said jet emanator means directs at least one of said high velocity fluid jet(s) towards said inflow means and said outflow means.

3. A method of macerating thrombus or other unwanted material in a body vessel or cavity, comprising the steps of:
   a. providing an elongated device having a first tube residing within and extending along the length of a second tube, said first tube having at its distal end jet emanator means for directing at least one high velocity fluid jet, inflow means for passage of entrained blood or other fluid from the body vessel into said device second tube, outflow means for passage of fluid and entrained blood or other fluid from said second tube into the body vessel, said jet emanator means oriented so that at least one of said high velocity fluid jet(s) entrains and draws surrounding blood or other fluid from the body vessel or cavity through said inflow means and into said second tube, and said jet emanator means located with respect to said outflow means such that at least some fluid directed by said jet emanator means passes through said at least one outflow means;
   b. inserting said elongated device into a body vessel or cavity, and advancing said elongated device to a site of thrombus or other unwanted material in the body vessel or cavity;
   c. connecting said elongated device to a source of pressurized fluid so that fluid jet(s) emanate from said jet emanator means, entrains blood or other fluid which may contain thrombus or other unwanted material and draws the blood or other fluid into said second tube through said inflow means, and creates a pressurized region in said second tube which drives fluid and entrained blood or other fluid which may contain thrombus or other unwanted material out of said second-tube through said outflow means creating cross stream jet(s) of fluid and entrained blood or other fluid;
   d. using said elongated device to break apart thrombus or other unwanted material in the body vessel or cavity, where fluid forces from the cross stream jet(s) and a recirculation of fluid from said outflow means and back in through said inflow means and past said high velocity jet(s) macerates said thrombus or other unwanted material; and,
   e. using said elongated device to remove thrombus or other unwanted material from the body.

4. The method of claim 3, wherein said jet emanator means directs at least one of said high velocity fluid jet(s) towards said inflow means and said outflow means.

* * * * *

UNITED STATES PATENT AND TRADEMARK OFFICE
CERTIFICATE OF CORRECTION

PATENT NO. : 6,764,483 B1
DATED : July 20, 2004
INVENTOR(S) : Bonnette et al.

It is certified that error appears in the above-identified patent and that said Letters Patent is hereby corrected as shown below:

<u>Title page,</u>
Item [73], Inventors, "Steven E. Wiesel" should read -- Stephen E. Weisel --; and
"Robert C. Dutchner" should read -- Robert G. Dutcher --

Signed and Sealed this

Twenty-eighth Day of September, 2004

JON W. DUDAS
*Director of the United States Patent and Trademark Office*